(12) United States Patent
Varanasi et al.

(10) Patent No.: US 9,242,222 B2
(45) Date of Patent: Jan. 26, 2016

(54) ALDOSE-KETOSE TRANSFORMATION FOR SEPARATION AND/OR CHEMICAL CONVERSION OF C6 AND C5 SUGARS FROM BIOMASS MATERIALS

(75) Inventors: Sasidhar Varanasi, Toledo, OH (US); Patricia Relue, Toledo, OH (US); Bin Li, Toledo, OH (US)

(73) Assignee: The University of Toledo, Toledo, OH (US)

( * ) Notice: Subject to any disclaimer, the term of this patent is extended or adjusted under 35 U.S.C. 154(b) by 345 days.

(21) Appl. No.: 13/641,849

(22) PCT Filed: Apr. 19, 2011

(86) PCT No.: PCT/US2011/033030
§ 371 (c)(1),
(2), (4) Date: Nov. 12, 2012

(87) PCT Pub. No.: WO2011/133536
PCT Pub. Date: Oct. 27, 2011

(65) Prior Publication Data
US 2013/0074397 A1   Mar. 28, 2013

Related U.S. Application Data

(60) Provisional application No. 61/325,710, filed on Apr. 19, 2010.

(51) Int. Cl.
| | | |
|---|---|---|
| *C12P 19/24* | (2006.01) | |
| *B01J 19/00* | (2006.01) | |
| *C07H 1/08* | (2006.01) | |
| *C07H 3/02* | (2006.01) | |
| *C13K 13/00* | (2006.01) | |
| *C12M 1/12* | (2006.01) | |
| *C12M 1/00* | (2006.01) | |

(52) U.S. Cl.
CPC . *B01J 19/00* (2013.01); *C07H 1/08* (2013.01); *C07H 3/02* (2013.01); *C12M 25/18* (2013.01); *C12M 47/10* (2013.01); *C13K 13/007* (2013.01); *Y02E 50/17* (2013.01)

(58) Field of Classification Search
CPC ....... C07H 3/02; C13K 13/007; C12M 47/10; C12M 25/18; B01J 19/00; B01J 9/00; Y02C 50/17; Y02E 50/17
See application file for complete search history.

(56) References Cited

U.S. PATENT DOCUMENTS

| | | |
|---|---|---|
| 3,793,189 A | 2/1974 | Corbett |
| 4,069,104 A | 1/1978 | Barker et al. |
| 4,273,922 A * | 6/1981 | Hicks ........................... 536/125 |
| 4,490,468 A | 12/1984 | Gong et al. |
| 5,241,087 A | 8/1993 | van Eikeren |
| 5,254,468 A | 10/1993 | Fournier et al. |
| 5,397,700 A | 3/1995 | Fournier et al. |
| 5,800,624 A | 9/1998 | Smith et al. |
| 5,840,677 A | 11/1998 | Nielsen et al. |
| 6,022,477 A | 2/2000 | Luo et al. |
| 7,037,378 B2 | 5/2006 | Jumppanen et al. |
| 7,674,608 B2 | 3/2010 | Varanasi et al. |
| 8,217,211 B2 | 7/2012 | Agrawal et al. |
| 8,507,232 B2 | 8/2013 | Varanasi et al. |
| 8,927,240 B1 | 1/2015 | Maddi et al. |
| 2008/0227162 A1 | 9/2008 | Varanasi et al. |
| 2008/0241818 A1* | 10/2008 | Lappalainen et al. ............ 435/5 |
| 2008/0318284 A1* | 12/2008 | Soong et al. .................... 435/96 |
| 2009/0011473 A1 | 1/2009 | Varanasi et al. |
| 2009/0082604 A1 | 3/2009 | Agrawal et al. |
| 2009/0090046 A1 | 4/2009 | O'Connor et al. |
| 2009/0139137 A1 | 6/2009 | Ikura et al. |
| 2009/0275098 A1 | 11/2009 | Beatty et al. |
| 2009/0305935 A1 | 12/2009 | Cascao-Pereira et al. |
| 2010/0004437 A1 | 1/2010 | Binder et al. |
| 2010/0269990 A1 | 10/2010 | Dottori et al. |
| 2010/0285552 A1 | 11/2010 | Varanasi et al. |
| 2011/0294163 A1* | 12/2011 | Li et al. .......................... 435/72 |
| 2013/0074397 A1 | 3/2013 | Varanasi et al. |

FOREIGN PATENT DOCUMENTS

| | | |
|---|---|---|
| WO | 2005/056808 A2 | 6/2005 |
| WO | WO 2009089103 A1 * | 7/2009 |

OTHER PUBLICATIONS

Olivier et al. Biotechnol. Bioengineer. (1986) 28: 684-699.*
Dukler et al. Biotechnol. Biopengineer. (2001) 75(1): 25-28.*
Griffin et al. J. Chem. Technol. Biotechnol. (2004) 79: 505-511.*
Hsiao et al. Enzyme Microb. Technol. (1982) 4: 25-31.*
Sigma website for Aliquat 335 downloaded from http://www.sigmaaldrich.com/catalog/product/aldrich/205613?/lang=en&region=US on Feb. 9, 2015.*
Di Luccio et al. Desalination (2002) 148: 213-220.*
Johnson et al. Innovative Food Sci. Emerging Technol. (2009) 10: 616-620.*
Altamore et al., "Cavitand Boronic Acids Mediate Highly Selective Fructose Transport", Organic Letters, 2002, vol. 4, No. 20, pp. 3489-3491.
Andersson et al., "Effect of Different Carbon Sources on the Production of Succinic Acid Using Metabolically Engineered *Escherichia coli*", Biotechnology Progress, 2007, vol. 23, pp. 381-388.
Bridgwater, "Renewable Fuels and Chemicals by Thermal Processing of Biomass", Chemical Engineering Journal, 2003, vol. 91, pp. 87-102.
Byers et al., "A Feasibility Analysis of a Novel Approach for the Conversion of Xylose to Ethanol", Chemical Engineering Communications, 1992, vol. 112, No. 1, pp. 165-187, Abstract Only.

(Continued)

*Primary Examiner* — Susan Hanley

(74) *Attorney, Agent, or Firm* — MacMillan, Sobanski & Todd, LLC

(57) ABSTRACT

Systems for converting aldose sugars to ketose sugars and separating and/or concentrating these sugars using differences in the sugars' abilities to bind to specific affinity ligands are described.

40 Claims, 6 Drawing Sheets

(56) References Cited

OTHER PUBLICATIONS

Chiang et al., "d-Xylulose Fermentation to Ethanol by *Saccharomyces cerevisiae*", Applied and Environmental Microbiology, 1981, vol. 42, No. 2, pp. 284-289.

Chiang et al., "Enzymatic and Microbial Preparation of D-Xylulose from D-Xylose", Applied and Environmental Microbiology, 1981, vol. 42, No. 1, pp. 66-69.

Dadi et al., "Enhancement of Cellulose Saccharification Kinetics Using an Ionic Liquid Pretreatment Step", Biotechnology and Bioengineering, 2006, vol. 95, No. 5, pp. 904-910, Abstract Only.

Demirbas, "Biorefineries for Biofuel Upgrading: A Critical Review", Applied Energy, 2009, vol. 86, pp. S151-S161.

Dote et al., "Recovery of Liquid Fuel From Hydrocarbon-rich Microalgae by Thermochemical Liquefaction", Fuel. 1994, vol. 73, No. 12, pp. 1855-1857.

Fournier et al., "Demonstration of pH Control in a Commerial Immobilized Glucose Isomerase", Biotechnology and Bioengineering, 2000, vol. 52, No. 6, pp. 718-722, Abstract Only.

Grierson et al., "Thermal Characterisation of Microalgae under Slow Pyrolysis Conditions", Journal of Analytical and Applied Pyrolysis, 2009, vol. 85, pp. 118-123.

Inloes et al., "Ethanol Production by *Saccharomyces cerevisiae* Immobilized in Hollow-Fiber Membrane Bioreactors", Applied and Environmental Microbiology, 1983, vol. 46, No. 1, pp. 264-278.

João Miguel de Sousa André, "Mixed Matrix Membranes—A new platform for enzymatic reactions", Dissertation, 2009.

Lee et al., "Effects of Medium Components on the Growth of Anaerobiospirillum succiniciproducens and succinic acid production", Process Biochemistry, 1999, vol. 35, pp. 49-55.

Mata et al., "Microalgae for Biodiesel Production and Other Applications: A Review", Renewable and Sustainable Energy Reviews, 2009, pp. 1-16.

Miao et al., "Fast Pyrolysis of Microalgae to Produce Renewable Fuels", Journal of Analytical and Applied Pyrolysis, 2004, vol. 71, pp. 855-863.

Olivier et al., "Sugar Cane Bagasse as a Possible Source of Fermentable Carbohydrates. II. Optimization of the Xylose Isomerase Reaction for Isomerization of Xylose as well as Sugar Cane Bagasse Hydrolyzate to Xylulose in Laboratory-Scale Units", Biotechnology and Bioengineering, 1986, vol. 28, pp. 684-699.

Peng et al., "Effects of Temperature and Holding Time on Production of Renewable Fuels from Pyrolysis of Chlorella protothecoides", Journal of Applied Phycology, 2000, vol. 12, pp. 147-152.

Rao et al., "A Novel Technique that Enables Efficient Conduct of Simultaneous Isomerization and Fermentation (SIF) of Xylose", Applied Biochemistry and Biotechnology, 2008, vol. 146, pp. 101-117.

Rao et al., "Enhanced Ethanol Fermentation of Brewery Wastewater Using the Genetically Modified Strain *E. coli* KO11", Applied Microbiology and Biotechnology, 2007, vol. 74, pp. 50-60.

Ross et al., "Classification of Macroalgae as Fuel and its Thermochemical Behaviour", Bioresource Technology, 2008, vol. 99, pp. 6494-6504.

Ross et al., "Investigation of the Pyrolysis Behaviour of Brown Algae before and after Pre-treatment using PY-GC/MS and TGA", Journal of Analytical and Applied Pyrolysis, 2009, vol. 85, pp. 3-10.

Westmark et al., "Selective Monosaccharide Transport through Lipid Bilayers Using Boronic Acid Carriers", Journal of the American Chemical Society, 1996, vol. 118, pp. 11093-11100.

Wyman, "Ethanol from Lignocellulosic Biomass: Technology, Economics, and Opportunities", Bioresource Technology, 1994, vol. 50, pp. 3-16.

Yuan et al., "A Viable Method and Configuration for Fermenting Biomass Sugars to Ethanol Using Native *Saccharomyces cerevisiae*", Bioresource Technology, 2012, vol. 117, pp. 92-98.

Chinese 1st Office Action, Application No. 200980103397.4 dated Nov. 2, 2011.

PCT International Preliminary Report on Patentability, PCT/US2009/030033 filed Jan. 2, 2009, dated Jul. 15, 2010.

PCT International Search Report and the Written Opinion, PCT/US2009/030033 filed Jan. 2, 2009, dated 102 Mar. 2009.

PCT International Search Report and the Written Opinion, PCT/US2011/033030 filed Apr. 19, 2011, dated Aug. 26, 2011.

\* cited by examiner

ALDOSE-KETOSE TRANSFORMATION FOR SEPARATION AND/OR CHEMICAL CONVERSION OF C6 AND C5 SUGARS FROM BIOMASS MATERIALS

CROSS-REFERENCE TO RELATED APPLICATIONS

This application claims the benefit of PCT application No. PCT/US11/033030 filed Apr. 19, 2011, which claims priority to U.S. provisional application, Ser. No. 61/325,710 filed Apr. 19, 2010, the entire disclosure of which is expressly incorporated herein by reference.

STATEMENT REGARDING FEDERALLY SPONSORED RESEARCH

This invention was made with government support under GO18163 awarded by the Department of Energy. The government has certain rights in the invention.

BACKGROUND

Mixed sugar streams, particularly those containing both C5 and C6 sugars, result from hydrolysis of lignocellulosic biomass. Following hydrolysis, these sugars mainly exist in the aldose form. However, ketose isomers of these sugars are typically more amenable to further conversion to useful products and fuels. For example, furans, which form precursors for polymers and hydrocarbon fuels (that could replace gasoline) can be made more easily from the ketose sugars than aldose isomers, and similarly, ethanol can be produced by native yeast through the fermentation the C5 sugar xylose only in its keto-isomer (xylulose) form. As a result, the sugars contained in biomass hydrolysate may need to be converted to their ketose form to facilitate their chemical conversion. The necessary isomerization of aldose to ketose can be achieved by enzymatic (glucose/xylose isomerase (XI)) or chemical (solid acid/base) catalysis. However, the reaction generally favors the aldose form of the sugar and, at equilibrium, only a small portion of the sugar is in the ketose form.

It would be useful to have a system for providing an efficient aldose-ketose transformation and/or separation of C5 and C6 sugars from biomass materials.

SUMMARY

Systems for converting aldose sugars to ketose sugars and separating and/or concentrating these sugars using differences in the sugars' abilities to bind to specific affinity ligands are described.

In a broad aspect, there are provided systems for converting aldose sugars to ketose sugars and separating and/or concentrating these sugars. In general, the system includes using differences in the sugars' abilities to bind to specific affinity ligands.

In a broad aspect, there is provided herein system for converting an aldose sugar to its ketose sugar, comprising:

a) contacting a C5 and/or C6 aldose sugar present in a saccharified hydrolysate with a catalyst to form a ketose isomer of the C5 and/or C6 sugar;

b) contacting isomerized ketose C5 and/or C6 sugar with a complexing agent (CA) to form to a ketose-CA conjugate; the CA have a binding affinity more specific to the ketose sugar compared to the aldose sugar;

c), optionally, repeating steps a) and b) to provide a concentrated hydrolysate having more ketose-CA conjugate than aldose sugar; and d) isolating ketose sugar from the ketose-CA conjugate in the concentrated hydrolysate; and e) recovering the ketose sugar.

In certain embodiments, the system includes removing ketose from hydrolysate to overcome an unfavorable equilibrium ratio of aldose:ketose (e.g., xylose:xylulose). Also, in certain embodiments, the aldose sugars are present in lignocellulosic biomass hydrolysates.

In certain embodiments, the ketose sugars are isolated by: lowering pH of the concentrated hydrolysate to effect the release of the ketose from the ketose-CA conjugate; and converting the CA to a lipophilic conjugate acid form.

In certain embodiments, wherein the saccharified hydrolysate has a pH between about 7.5 to about 9 when the catalyst comprises xylose isomerase (XI).

In certain embodiments, the saccharified hydrolysate has a pH between about 7.5 to about 11 when the catalyst comprises a zeolite catalyst.

In certain embodiments, the CA is present in an immiscible organic phase that is physically separated by a permeable device from the isomerized hydrolysate, and the permeable device allows transport of the CA into (and out of) the isomerized hydrolysate, while substantially preventing transport of the immiscible organic phase.

In certain embodiments, the immiscible organic material comprises one or more of as ethyl acetate, dichloromethane, o-nitrophenyl octyl ether (NPOE), and or diethyl ether.

In certain embodiments, the system can include: passing the hydrolysate through a packed bed reactor containing an immobilized xylose isomerase (XI) or zeolite catalyst, where xylose present as the aldose sugar in the hydrolysate is converted to its ketose isomer, xylulose.

In certain embodiments, the CA is present in an organic phase, the xylulose extracting the complexing agent (CA) from the organic phase via ester formation with a conjugate base form of the CA.

In certain embodiments, the system can include extracting the CA from the organic phase and allowing the ester formation until nearly all of the xylose is isomerized.

In certain embodiments, the system includes:

acidifying the isomerized hydrolysate containing the ketose-CA conjugate to a pH that favors the conjugate acid form of the CA, such that the conjugate acid form of the CA dissociates from the ketose, and the dissociated ketose increases the hydrophobicity of the CA in the isomerized hydrolysate, and driving the conjugate acid form of the CA back into the organic phase, thereby forming a CA-depleted/ketose-rich hydrolysate.

In certain embodiments, the system includes: acidifying the CA-depleted/ketose-rich hydrolysate to a pH at which the ketose sugar can be fermented to ethanol by $S.$ $cerevisiae$, or other native microorganisms.

In certain embodiments, the system can include driving the hydrophobic CA back into the organic phase to form a CA-enriched organic phase, and contacting the CA-enriched organic phase with a fresh batch of saccharified hydrolysate.

In certain embodiments, the system can include: immobilizing the complexing agent (CA) to a support material.

In certain embodiments, one or more of the CA, the pH and temperature of the hydrolysate, are altered to select for one or more specific sugars.

In certain embodiments, the system can include: selecting the CA such that, at selected pH and temperature conditions, the CA mainly binds to xylulose, and not binds any appreciable amounts of glucose, xylose or fructose.

In certain embodiments, the system can include: circulating the hydrolysate through at least a first column comprised of a packed bed of immobilized xylose isomerase (XI) or zeolite catalyst, and through a vessel having a CA-enriched material therein. It is to be understood, that in certain embodiments, this can include the immobilized C; and, in certain embodiments, a hollow fiber module with a CA-organic phase.

In certain embodiments, the system can include: circulating the hydrolysate through at least a first column comprised of a packed bed of immobilized xylose isomerase (XI) or zeolite catalyst particles, and through a second column comprised of a packed bed of a complexing agent (CA) immobilized on a support material.

In certain embodiments, as the hydrolysate passes through the XI column, xylose and a portion of glucose present in the hydrolysate are converted to corresponding keto-isomers (xylulose and fructose, respectively).

In certain embodiments, as the hydrolysate mixture is routed through the immobilized CA column, mainly the ketose will complex with bound CA sites, thereby lowering free ketose concentration in the hydrolysate.

In certain embodiments, the system can include: circulating the hydrolysate through two-columns connected in series. In certain embodiments, the system can include: isolating the immobilized CA column and flushing the immobilized CA column with a carrier solution of low pH sufficient for bound ketose to be released from the CA and to accumulate in the low pH carrier solution. In certain embodiments, the pH is about 4.0 to about 4.5. Further, in certain embodiments, the pH can corresponds to a pH of a fermentation medium suitable for converting xylulose to ethanol by native *S. cerevisiae*, or other native microorganisms.

In certain embodiments, the system can include: regenerating the immobilized CA column and reusing with a fresh batch of hydrolysate.

In certain embodiments, the system can include: controlling a volume of the low pH carrier sufficient to recover the ketose as a "concentrated" solution.

In certain embodiments, the system can include: separating the xylose from other C6 sugars as its keto-isomer and allowing for the recovery of xylulose as a concentrated solution.

In certain embodiments, the system can include: a lipophilic salt with the complexing agent (CA) in the organic phase, and extracting the ketose out of the organic phase.

In certain embodiments, the system can include: passing the isomerized hydrolysate and the CA containing organic phase through a hollow fiber contained liquid membrane contactor (HFCLMC).

In certain embodiments, the complexing agent (CA) comprises a complexing agent soluble in organic solvents and/or capable of being covalently-bound to a solid substrate.

In certain embodiments, the complexing agent (CA) comprises one or more of aryl boronic acids (ABAs), including, but not limited to PBA, 3aPBA, 4cPBA and 4-biphenylboronic acid,

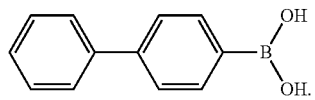 [SMILES: OB(O)c1ccc(-c2ccccc2)cc1]

In certain embodiments, the complexing agent (CA) comprises one or more aryl boronic acids (ABA), Ar—B(OH)$_2$, where Ar represents unsubstituted or substituted "aryl" group.

In certain embodiments, the aryl boronic acids (ABA), comprise one or more of the following aryl groups: 4-MeC$_6$H$_4$—, where Me is methyl; 2-iPrC$_6$H$_4$—, where iPr is isopropyl; 2-naphthyl, 3-BnOC$_6$H$_4$—, where Bn is benzyl; 4-MeO$_2$CC$_6$H$_4$—, where Me is methyl; and 4-pyridinyl.

In certain embodiments, one or more functional groups such as NH$_2$ or COOH are incorporated into the aryl group to enable covalent bonding of the aryl boronic acids to a functionalized support. Further, in certain embodiments, functionalization of the support includes one or more of: oxirane, amine, carboxyl or other complementary groups that covalently attaches to the functional group on the aryl boronic acid.

In certain embodiments, the ABA comprises a hydrophobic substituted aryl boronic acid. Non-limiting examples include wherein the ABA comprises:

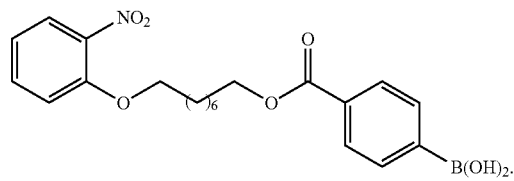

In certain embodiments, the hydrophobic substituted aryl boronic acid is used in a liquid-liquid extraction followed by stripping or HFCLMC implementation.

In certain embodiments, the ABA comprises a compound that exhibits a higher selectivity toward ketose binding compared to monoboronic acids.

In certain embodiments, the ABA comprises a multi-dentate boronic acid carrier.

In certain embodiments, the ABA compound comprises one or more of:

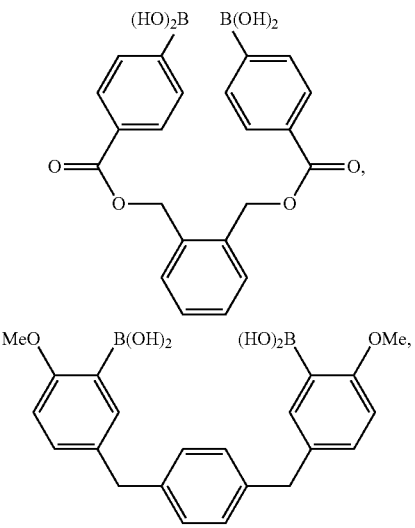

-continued

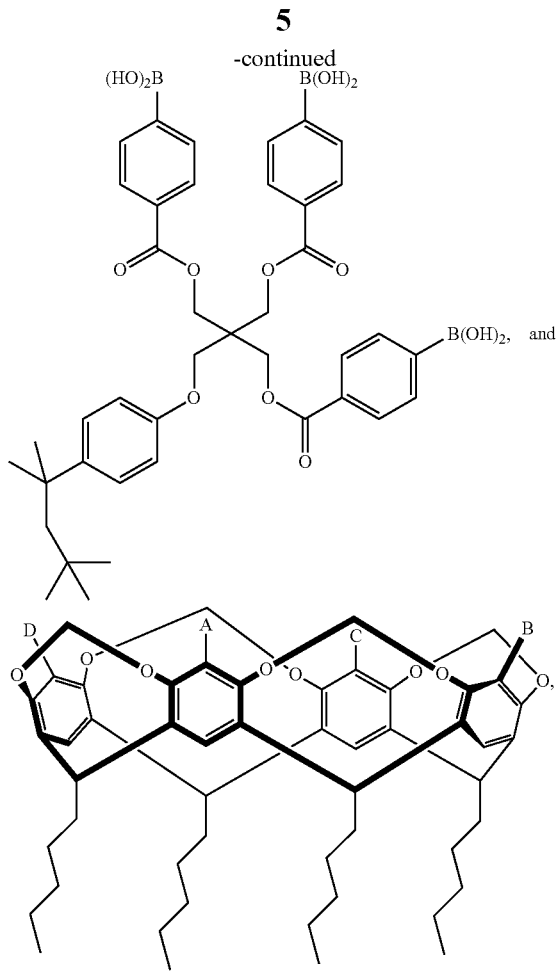

wherein A and C are B(OH)$_2$ and B and D are H groups.

In certain embodiments, the complexing agent (CA) comprises one or more unsubstituted or organosubstituted germanate compounds.

In certain embodiments, the CA is contained in a holding vessel that includes a contacting device that physically separates the hydrolysate from the organic phase while allowing movement of the CA into and out of the hydrolysate. Further, in certain embodiments, the contacting device can comprise a CA permeable membrane. Also, in certain embodiments, the contacting device can comprise a microporous hollow fiber contactor.

In certain embodiments, the system can be as shown in FIG. 2 and used for separating xylose (in the form of its keto-isomer, xylulose) from a biomass hydrolysate containing a mixture of glucose and xylose.

In a particular aspect, there is provided herein a system for converting an aldose in a biomass hydrolysate to its ketose isomer and for making the ketose available for fermentation reactions at an appropriate pH, comprising:

1a) adjusting a pH of a saccharified biomass hydrolysate containing one or more aldose sugars to a value between about 7.5 and about 11;

1b) contacting the pH-adjusted-hydrolysate of step 1a) with a catalyst where at least a portion of the aldose sugar in the pH-adjusted-hydrolysate is converted to its ketose isomer;

2a) contacting the ketose isomer in the isomerized-hydrolysate of step 1b) with a complexing agent (CA) to form a ketose-conjugate base form of the CA;

2b) optionally, repeating steps 1)-2a) as needed, until a desired concentration of the aldose in the isomerized-hydrolysate is converted into an esterified ketose-CA conjugate;

3) ceasing the isomerization cycle of steps 1a)-2b);

4) separating the esterified ketose-CA conjugate from the isomerized-hydrolysate by acidifying the isomerized-hydrolysate to a pH (optionally, between about pH 2 to about 4.5) that favors formation of a conjugate acid form of the CA, causing the CA to dissociate from the ketose; and, 5) contacting the ketose-rich hydrolysate of step 4) with CA-depleted organic material, causing the dissociated CA to be separated from the ketose-rich hydrolysate; and optionally, 6) recovering the dissociated CA material and returning to the organic material of step 2a).

In certain embodiments, the ketose present in the isomerized hydrolysate extracts the CA from the organic material via ester formation with a conjugate base form of the CA, thereby shifting the aldose/ketose equilibrium in favor of more ketose formation in the isomerized hydrolysate.

In certain embodiments, the system can be as shown in FIG. 3 and used for separating xylose (in the form of its keto-isomer, xylulose) from a biomass hydrolysate containing a mixture of glucose and xylose.

In another aspect, there is provided herein a system for converting an aldose in a biomass hydrolysate to its ketose isomer and for making the ketose available for fermentation reactions at an appropriate pH, comprising:

incorporating an immobilized xylose isomerase XI (or solid acid/base catalyst) column in an extraction step, converting xylose to xylulose at high yield and high selectivity over glucose to fructose, and separating xylulose from glucose by binding xylulose to an aryl boronic acid.

In yet another aspect, there is provided herein a system for converting an aldose in a biomass hydrolysate to its ketose isomer and for making the ketose available for fermentation reactions at an appropriate pH, comprising:

1a) adjusting a pH of a saccharified biomass hydrolysate containing one or more aldose sugars to a value between about 7.5 and about 11;

1b) contacting the pH-adjusted-hydrolysate of step 1a) with a catalyst where at least a portion of the aldose sugar in the pH-adjusted-hydrolysate is converted to its ketose isomer;

2) contacting the ketose isomer in the isomerized-hydrolysate of step 1b) with a complexing agent (CA) to form a ketose-conjugate base form of the CA; wherein the contacting comprises 3) bringing the isomerized hydrolysate from the packed bed reactor into contact with an immiscible organic phase that dissolves the CA and a lipophilic salt (such as a quaternary ammonium salt QX); and allowing the ketose in the isomerized hydrolysate to be extracted into the organic phase via ester formation with a conjugate base form of the CA that is coupled to an ion pair formation with $Q^+$, thus reducing the concentration of uncoupled ketose in the hydrolysate, and shifting the aldose/ketose equilibrium in favor of more ketose formation;

4) preparing an aqueous medium having a pH is in the range of about 2 to about 4.5 that contains an acid HX (where X is the same anion as that of the lipophilic salt) for stripping of the xylulose from the organic phase generated in step 3;

5) bringing the low pH aqueous medium into contact with the ketose-rich organic phase from step 3); wherein, at the low pH, the both ketose and hydroxyl ion are released into the aqueous phase and the CA is converted to its non-ionic conjugate acid; and, wherein, at the same time, the $Q^+$ ion that formed the ion pair combines with an X⁻ ion from the aqueous medium to re-form the lipophilic salt; and 6) recovering the ketose from the ketose-rich organic phase.

In certain embodiments, the system can include: controlling the volume of the aqueous medium such that the concentration of ketose is higher than the initial concentration of aldose in the hydrolysate.

In certain embodiments, the system can include: reusing the regenerated organic phase containing the CA and the lipophilic salt for a next batch of hydrolysate.

In another aspect, there is provided herein a system substantially as shown in FIG. 4 and used for separating xylose (in the form of its keto-isomer, xylulose) from a biomass hydrolysate containing a mixture of glucose and xylose.

In certain embodiments, the system can include: combining the isomerization step with the selective simultaneous extraction step using a hollow fiber contained liquid membrane contactor (HFCLMC) system.

In certain embodiments, the HFCLMC system comprises a shell having a first set of porous hollow fibers adapted for carrying isomerized hydrolysate; and a second set of porous hollow fibers adapted for carrying an aqueous medium. The shell can be configured for containing the organic extraction phase in a shell-side space substantially surrounding the first and second sets of fibers. In certain embodiments, the separate sets of microporous hollow fibers are commingled within the shell.

In certain embodiments, the xylulose is transported from a high pH medium to a low pH medium across the contained organic liquid membrane, wherein the transport of xylulose is facilitated through the organic film by the dissolved CA and QX combination.

In certain embodiments, the wherein saccharified biomass hydrolysate containing glucose and xylose is passed through a packed bed reactor containing immobilized xylose isomerase (XI) or solid acid/base catalyst;

the isomerized hydrolysate flowing through the first set of fibers within the HFCLMC, the isomerized hydrolysate coming into contact with the immiscible organic phase containing lipophilic CA and a lipophilic salt (QX), that fills the shell;

the xylulose in the isomerized hydrolysate being extracted into the organic phase via ester formation with a conjugate base form of the CA coupled to ion pair formation with Q⁺, thus reducing concentration xylulose in the hydrolysate, and shifting the xylose/xylulose equilibrium in favor of more xylulose formation;

the low pH aqueous medium having an acid HX (where X is the same anion as that of the lipophilic salt (QX) concurrently flows through the second set of fibers and also contacts the organic phase contained on the shell side; the xylulose and hydroxyl ion are released into the aqueous phase and the CA is re-converted to its non-ionic conjugate acid; and the Q⁺ ion, which formed the ion pair, combines with an X⁻ ion in the aqueous medium to re-form the lipophilic salt.

In certain embodiments, the system can include: immobilizing the complexing agent CA to a solid support material, such that the immobilized CA acts as a solid-phase extraction medium.

In certain embodiments, the system can include: selecting a CA having a property to enhance selectivity for a specific sugar.

In certain embodiments, the system can include: removing the bound sugar from the hydrolysate medium by contacting the support material with a lower pH solution to achieve separation from the hydrolysate.

In another aspect, there is provided herein a system substantially as shown in FIG. 5 for separating xylose (in the form of its keto-isomer, xylulose) from a biomass hydrolysate containing a mixture of glucose and xylose.

In an other aspect, there is provided herein a system of separating xylose (in the form of its keto-isomer, xylulose) from a biomass hydrolysate containing a mixture of glucose and xylose; comprising:

circulating the biomass hydrolysate through a first column comprised of a packed bed of immobilized xylose isomerase (XI) or solid acid/base catalyst particles; and a second column comprised of a packed bed of a complexing agent (CA) immobilized on a support material; the CA and its binding chemistry to the support material being chosen that the CA substantially binds to xylulose, and not in any appreciable amounts to glucose, xylose or fructose;

passing the hydrolysate through the first (XI) column 51 such that, xylose and a portion of glucose are converted to their corresponding keto-isomers (xylulose and fructose, respectively);

passing the isomerized hydrolysate through the immobilized CA second column 52, wherein the xylulose complexes with bound CA sites, thereby lowering the xylulose concentration in the hydrolysate, and the reduction in concentration of non-bound xylulose in the isomerized hydrolysate drives the isomerization reaction in the direction of more xylulose formation; and optionally, isolating the second immobilized CA column and contacting the second (CA) column with a low pH carrier medium, so the bound xylulose is released from the CA sites and accumulates in the low pH carrier medium.

In certain embodiments, the system can further including controlling the volume of the low pH aqueous solution such that xylulose concentration in the recovered stream is higher than the xylose concentration in the original hydrolysate.

Further, in certain embodiments, the system can include an immobilized CA column to recover both glucose and xylose from the hydrolysate by binding glucose and xylose to appropriately chosen CA, and recovering glucose and xylose from the hydrolysate, while leaving behind other inhibitory compounds in the biomass hydrolysate.

In another aspect, there is provided herein use of concentrated ketose streams formed using a system as described herein in a fermentation process to produce a fuel such as ethanol.

In another aspect, there is provided herein use of concentrated ketose streams formed using a system as described herein in a fermentation process to produce chemicals such as succinic and fumaric acids.

In another aspect, there is provided herein a fuel formed by a system as described herein.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

Figure 1:
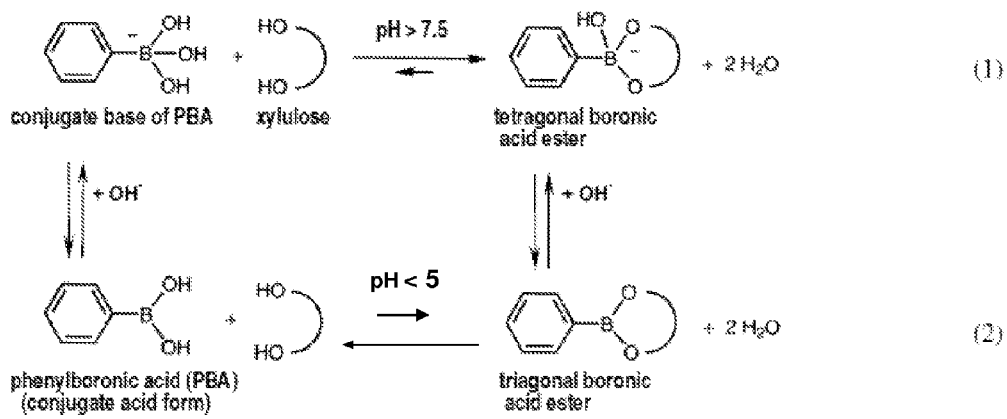
FIG. 1: Equilibrium formation of PBA-xylulose esters at high (Eq. 1) and low (Eq. 2) pH in water. This complexation ability of PBA with xylulose is used to drive the xylose-xylulose isomerization toward high conversion of xylose. Un-ionized PBA (bottom left) is able to preferentially partition into a water-immiscible organic solvent such as ethyl acetate. This forms the basis for its recovery from the aqueous sugar solution.

Described herein are methods for the transformation of aldose-ketose for the separation and/or chemical conversion of C6 and C5 sugars from biomass materials. In certain embodiments, the biomass materials are lignocellulosic biomass hydrolysate.

Provided herein is a method for improving yield of aldose-ketose transformations of biomass sugars; isomerization and separation of sugars; conversion of biomass sugars to ethanol with native yeasts.

Also provided herein is a lignocellulosic biomass refining process. Biofuels, biobased products, purified consumable sugars, purified high-value sugars can thus be produced by one or more of the systems, methods and apparatuses described herein.

The system described herein for concentrating sugars from biomass is less energy-intensive than conventional evaporation; moreover, concentrated sugars are obtained free of fermentation inhibitors present in the hydrolysate.

Following separation, the separated sugar/s is in a ketose form that is readily amenable to further biological and or chemical conversion.

In certain embodiments, the process can include recovering the separated sugars as concentrated solutions.

The resulting concentrated individual sugar streams are useful as initially recovered. The resulting concentrated individual sugar streams can be used for human and/or animal consumption.

Also, the resulting concentrated individual sugar streams are useful as feedstocks for production of fuels and chemicals.

In the system described herein the concentration of free xylulose in the hydrolysate is reduced, and there is a shift in the xylose/xylulose equilibrium in favor of more xylulose formation.

One class of sugar-binding, or complexing, agents (CA) include aryl boronic acids, $Ar-B(OH)_2$, where Ar represents an "aryl" group. For example,

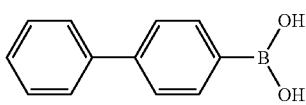

4-biphenylboronic acid or Ar=4-PhC$_6$H$_4$—

Other Ar groups can include, but are not limited to: 4-MeC$_6$H$_4$—, where Me is methyl; 2-iPrC$_6$H$_4$—, where iPr is isopropyl; 2-naphthyl, 3-BnOC$_6$H$_4$—, where Bn is benzyl; 4-MeO$_2$CC$_6$H$_4$—; 4-pyridinyl.

Functional groups such as NH$_2$ or COOH can be incorporated into the aryl group to enable covalent bonding of the aryl boronic acids to functionalized supports. Functionalization of the support can include oxirane, amine, aldehyde, carboxyl or other complementary groups that can covalently attach to the functional group on the aryl boronic acid.

Another more hydrophobic substituted aryl boronic acid that is particularly useful in liquid-liquid extraction followed by stripping or HFCLMC implementation is the compound shown below:

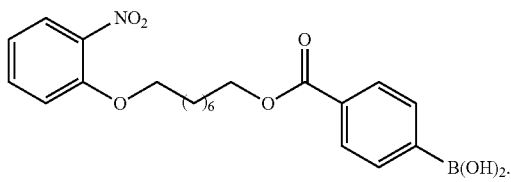

Compounds that may exhibit higher selectivity toward ketose binding compared to monoboronic acids are multidentate boronic acid carriers. Several examples of these compounds are shown in the structures below.

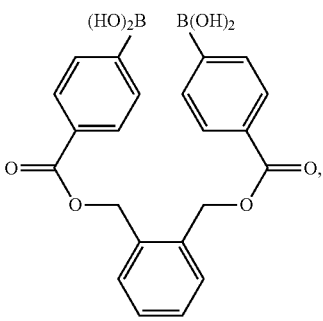

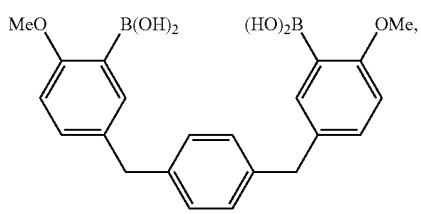

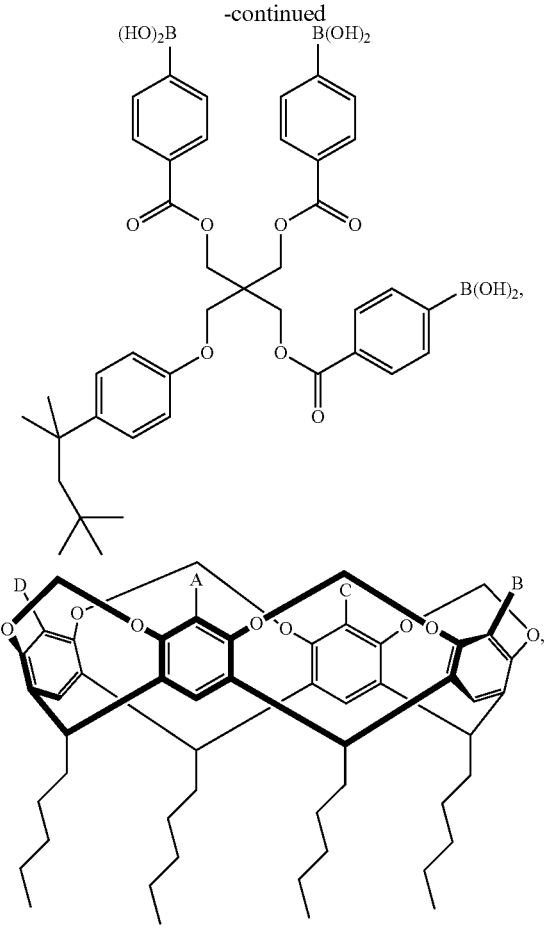

For the last structure on the above, A and C are B(OH)$_2$ and B and D are H groups.

All the mono and multidentate structures described above are based on the affinity of boronate compounds towards sugars. As shown in one of our examples, germanates are also able to bind selectively to ketose sugars. Thus, chemistries that replace boronate with germanate will also form suitable complexing agents for implementation of the methods described herein.

In the methods described herein, the selective affinity of ketoses to complexing agents is now used to produce high ketose yields, while simultaneously allowing recovery and reuse of the complexing agent and the isomerization catalyst. In addition, in certain embodiments, the method is useful for sugar separation and/or concentration.

While enzyme-catalyzed biochemical means of affecting aldose-ketose transformation has been described in the examples herein, it is to be understood that the isomerization can also be achieved through chemical means at elevated pH and or elevated temperatures where the aldose-ketose selectivity of CAs can be much higher, enabling higher ketose yields as well as better separation of ketose from aldose, using one or more of the methods described herein.

Thus, in a non-limiting manner, in the examples herein, the isomerization and separations were done at 50° C. and at 34° C., and it was observed that XI shows several orders of magnitude higher catalytic performance towards aldose-ketose conversion of C5 sugars compared to C6 sugars in this temperature range. This preference for C5 sugars can also be seen at higher temperatures (for example, at temperatures up to about 60° C.).

Method I:

Shifting the Aldose/Ketose Isomerization Reaction to Achieve High Ketose Yields

Phase Switching:

Borax, aryl boronic acids (ABA) and their derivatives, multidentate boronic acids and other oxyanion compounds can act as complexing agents (CA) by preferentially binding with the ketose forms of both C5 and C6 sugars.

One class of complexing agents that can exhibit pH-dependent partitioning between aqueous and organic phases is aryl boronic acids (ABAs). At high pH (>7.5), ABAs exist predominantly in their conjugated base form (see equations (1) and (2) in FIG. 1). The conjugated base is able to bind with polyols to form a tetragonal ester that is significantly more water soluble than the conjugated base form. However, when the pH of the aqueous medium is low (<5), the ABAs exist predominantly in the un-ionized conjugate acid form which is not able to complex effectively with polyols. Accordingly, the acid form has much lower water solubility and displays higher affinity to aprotic solvents. This pH-dependent complexation of ABAs to polyols and the resulting hydrophobic/hydrophilic transition provides a method of recovering the ABAs through a two-phase extraction scheme. As used herein, "phase-switch" refers to the pH dependent shuttling of the CA between the aqueous and organic phases.

Implementation of Method I—Phase-Switching of CA

In general, the isomerization of aldose to ketose can be been achieved using the enzyme catalyst xylose isomerase (XI) in the pH of 7.5-9.0. Also, solid-state acid/base catalysts can be used for aldose to ketose transformation. Examples of the basic-type catalysts include carbonate and hydroxide forms of hydrotalcite and cation-exchanged hydrotalcites and zeolites. Tin-containing zeolites are solid acid catalysts that can be used for isomerization of glucose to fructose in water. Certain advantages of zeolite catalysts over enzyme catalysts include: (1) relativity inexpensive inorganic compounds; (2) wider range of temperature and pH operating conditions as well as longer lifetimes; (3) faster reaction rates; and (4) increased resistance to impurities.

However, regardless of the nature of the catalyst, the aldose/ketose isomerization does not have a favorable equilibrium.

Although XI is capable of converting xylose to xylulose, under conditions where XI has significant activity, the equilibrium ratio of xylose:xylulose is typically high (on the order of 5:1). Hence, xylose isomerization does not have a favorable forward equilibrium (see Eq. 3 below).

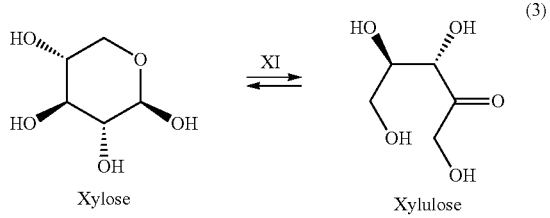

Xylose   Xylulose    (3)

One way to increase xylose conversion is to drive the isomerization forward by removal of the product xylulose. When the xylulose preferentially binds to the conjugate base of the ABA (see Eq. 1 in FIG. 1), the aldose/ketose equilibrium of the isomerization reaction is shifted in favor of more ketose formation.

Figure 2:
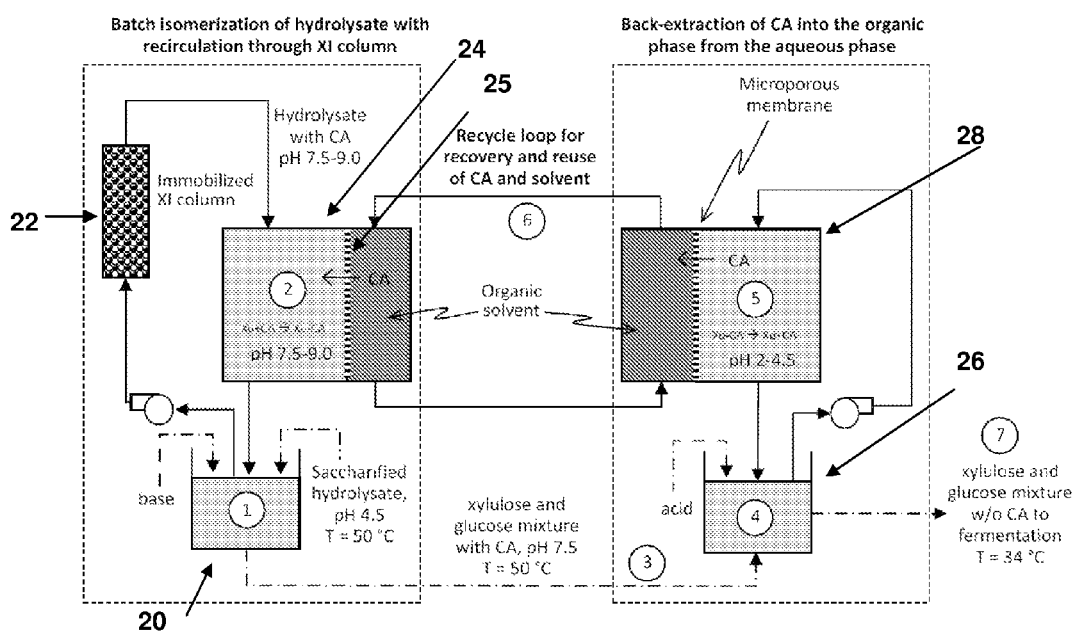
FIG. 2: Schematic diagram showing high yield xylose isomerization to xylulose (Xu) with phase-switching of the complexing agent (CA). Both the organic solvent and the complexing agent are recycled using a pH dependent extraction of the complexing agent between the organic and aqueous phases. Solid arrows indicate fluid flow paths; dashed arrows represent addition/withdrawal of material at a specific time.

The inventors herein have now developed a method to achieve high conversion of the xylose in biomass hydrolysate to its ketose isomer xylulose and make the sugar available to the fermentation reactions at an appropriate pH. FIG. 2 is a schematic representation of this strategy. Each of the steps in FIG. 2 is described more fully below:

FIG. 2—Step 1: Saccharified biomass hydrolysate 20 (at pH 4.5 and 50° C.), containing glucose and xylose, is filtered to remove lignin and other particulates and the pH is raised to a value between 7.5 and 9 through addition of a suitable base. The hydrolysate is passed through a packed bed reactor 22 containing immobilized xylose isomerase (XI) where xylose is converted to xylulose. For solid acid/base catalysts, the operational temperature (25-100° C.) and pH range (up to 11) is much broader than that of the XI enzyme.

FIG. 2—Step 2: The partially isomerized hydrolysate from the packed bed reactor 22 is brought into contact with an immiscible organic phase (such as ethyl acetate, dichloromethane, o-nitrophenyl octyl ether (NPOE) or diethyl ether) containing the complexing agent (CA), viz ABA, in a holding vessel 24 which includes a contacting device 25 that physically separates the hydrolysate from the organic phase while allowing transport of the CA between the two phases. In certain embodiments, the contacting device 25 can be a microporous hollow fiber contactor).

The xylulose formed in the isomerization reaction will extract the CA from the organic phase into the hydrolysate via ester formation with the conjugate base form of the CA. This, in effect, reduces the concentration of "free" xylulose in the hydrolysate, shifting the xylose/xylulose equilibrium in favor of more xylulose formation (see Eq. 3). As the hydrolysate repeatedly passes through the immobilized XI (or solid acid/base catalyst) column 22, the extraction of CA from the organic phase and ester formation in the aqueous phase continues until nearly all of the xylose is isomerized. With the solid acid/base catalyst, isomerization temperature and pH conditions are more flexible and can be set to allow for higher and more selective sugar binding to the CA.

FIG. 2—Step 3: At this stage, the isomerized hydrolysate (predominantly xylulose and glucose) is transferred to another vessel 26.

FIG. 2—Step 4: The hydrolysate is acidified to bring the pH down to 2 to 4.5; this pH favors the conjugate acid form of the CA, in which state it no longer associates with the xylulose and the ester breaks down (see FIG. 1 Eq. 2).

FIG. 2—Step 5: The acidified hydrolysate is pumped through another module 28 where it is brought into contact with the CA-depleted organic phase from Step 2, when the CA has been removed from the holding vessel 24. In the conjugate acid form, the CA is preferentially back-extracted into the organic phase, enriching the organic phase in CA.

FIG. 2—Step 6: The CA-laden organic phase from Step 5 can be sent back to the contacting device 25 in Step 2. Thus, the CA is extracted from the organic phase to the aqueous phase when the pH is high and is back-extracted into the organic phase from the aqueous phase when the pH is low. This "phase-switching" of CA is enhanced significantly in the presence of the ketose sugars at high pH. Phase-switching allows for the continuous recycling and reuse of both the organic phase and the CA.

FIG. 2—Step 7: Following the removal of the CA from the isomerized hydrolysate into the organic phase, the isomerized hydrolysate adjusted to a pH of 4.5 can be cooled to 34° C. and fermented to ethanol using native yeast. This cooling step can be integrated with other heating needs in the process to achieve thermal efficiencies.

Implementation of Method I—Interfacial Complexation

As the lipophilic character of the ABA increases, its ability to undergo phase-switching will diminish. However, it may still form a tetragonal boronic acid ester at the organic/aqueous interface and accumulate at the interface like a surfactant when the aqueous phase it contacts is at high pH. Nevertheless, binding of ABA to xylulose at the liquid-liquid interface will still effectively shift the xylose/xylulose equilibrium toward more xylulose formation. In such situations, there might be no phase-switching mechanism in operation. However, as shown in FIG. 2, the method can be modified to accommodate this situation.

For example, following completion of isomerization, the XI column is disconnected from the closed loop on the left side of FIG. 2 and the pH of the aqueous phase in the vessel 24 is lowered to effect the release of the sugar from the ABA and subsequent conversion of ABA to its lipophilic conjugate acid form. At the end of this step (as is the case after Step 5 of Method I Phase-Switching), the aqueous phase will be a mixture that is predominantly xylulose and glucose with minor amounts of fructose. Such a mixture is readily converted by native yeast into alcohol.

Method II—Simultaneous Aldose/Ketose Isomerization and Separation/Concentration of Pentose and Hexose Sugars Liquid-Liquid Extraction of Sugars:

ABA can be confined to the organic phase by adding lipophilic quaternary ammonium salts such as Aliquat® 336 ($Q^+X^-$) to the organic phase. As ABA in the organic phase approaches the high pH aqueous interface, it converts from conjugate acid to conjugate base form; in the conjugate base form it is able to bind readily with sugar at the aqueous/organic interface.

The lipophilic ammonium cation ($Q^+$) will form an ion pair with this tetragonal ABA-sugar ester anion, thereby extracting the tetragonal ester into the organic phase while the anion $X^-$ of Aliquat® 336 is liberated into the aqueous phase. Contacting the sugar-loaded organic phase with a low pH aqueous phase containing the acid HX enables stripping of the sugar back to the aqueous media with the uptake of $X^-$ into the organic phase as the co-anion of $Q^+$. In this mode of action, the ABA is facilitating the extraction of sugar from the aqueous phase into the organic phase while the ABA itself is confined to the organic phase. This is in contrast to the Method I Phase-Switching where the sugar is confined to the aqueous phase and the ABA is extracted from the organic phase into the aqueous phase and vice versa.

Unlike Method I, extraction of the sugar to a second phase with subsequent stripping can facilitate separation and concentration of sugar. In the past, immiscible liquid extraction was implemented in a two-step process, where in Step 1 xylose and/or glucose are extracted from a high-pH biomass hydrolysate into an organic phase, and in Step 2 the sugars are released into a low pH aqueous stripping solution. Until now, however; there has been no solution for the separation of the C6 from C5 sugars or for the separation of ketose from aldose sugars.

Figure 3:
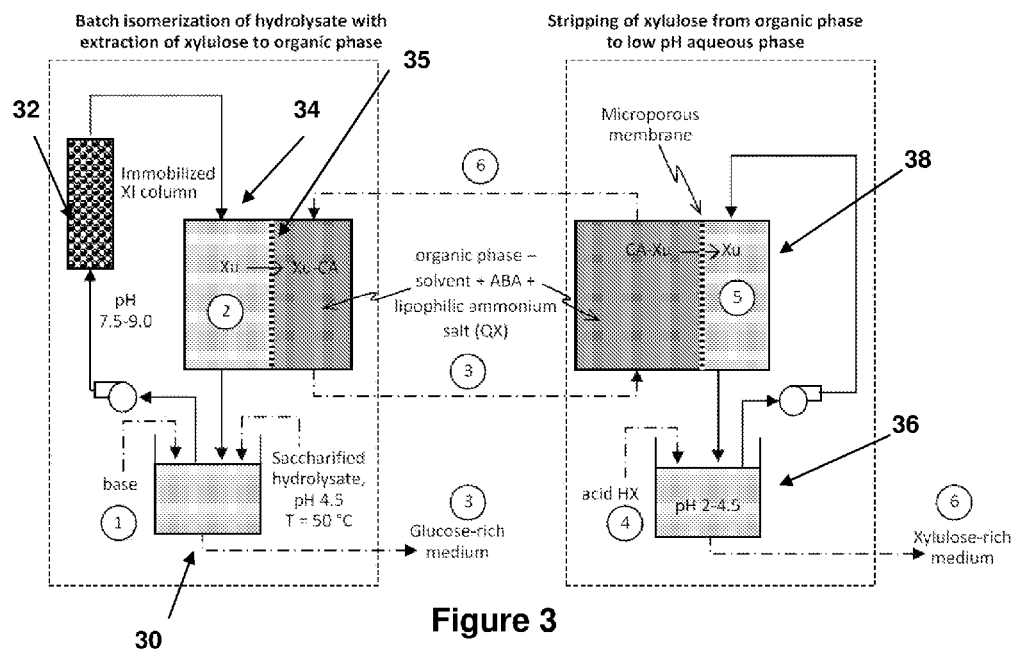
FIG. 3: Schematic diagram showing high yield xylose isomerization to xylulose with in-situ xylulose extraction. The high affinity of the CA for xylulose compared to aldose sugars (xylose and glucose) selectively extracts xylulose into the organic phase in Step 2, leaving behind a glucose-rich solution. Following isomerization, xylulose is stripped from the organic phase into a small volume of low pH aqueous media to recover a concentrated xylulose solution. The xylulose-depleted organic phase is recycled and reused. The process accomplishes high conversion of xylose to xylulose, while also separating xylulose from glucose and concentrating xylulose. Solid arrows indicate fluid flow paths; dashed arrows represent addition/withdrawal of material at a specific time.

Implementation of Method II—Isomerization Coupled to Selective Liquid-Extraction and Stripping FIG. 3 illustrates a method that incorporates an immobilized XI (or solid acid/base catalyst) column in the extraction step. This modification not only allows for converting xylose to xylulose at high yield and high selectivity over glucose to fructose, but also enables the separation of xylulose from glucose by exploiting its superior affinity to ABA for selective extraction. FIG. 3 is a schematic representation of this strategy. Each of the steps in FIG. 3 is described more fully below:

FIG. 3—Step 1: Saccharified biomass hydrolysate 30 (at pH 4.5 and 50° C.), containing glucose and xylose, is filtered to remove lignin and other particulates and the pH is raised to a value between 7.5 and 9 through addition of a suitable base. The hydrolysate is passed through a packed bed reactor 32 containing immobilized xylose isomerase (XI) (or solid acid/base catalyst) where xylose is converted to xylulose.

FIG. 3—Step 2: The partially isomerized hydrolysate from the backed be reactor 32 is brought into contact with an immiscible organic phase that dissolves a lipophilic ABA and a quaternary ammonium salt (QX, such as Aliquat® 336) in a holding vessel 34 that includes a contacting device 35 that physically separates the hydrolysate from the organic phase while allowing transport of the sugar between the two phases. In certain embodiments, the contacting device 35 can be a microporous hollow fiber contactor. As discussed in the liquid-liquid extraction of sugars, the xylulose formed in the isomerization reaction is extracted into the organic phase via ester formation with the conjugate base form of the CA, which then forms an ion pair with $Q^+$. This, in effect, reduces the concentration of "free" xylulose in the hydrolysate, shifting the xylose/xylulose equilibrium in favor of more xylulose formation (see Eq. 3).

As the hydrolysate repeatedly passes through the immobilized XI (or solid acid/base catalyst) column 32, the extraction of xylulose to the organic phase continues until nearly all of the xylose is isomerized. The XI enzyme catalyzes xylose/xylulose transformation at a rate one-to-two orders of magnitude faster than the glucose/fructose transformation. Hence, during the time required for xylose isomerization, glucose is minimally isomerized (e.g., see data in FIG. 8).

Figure 11:
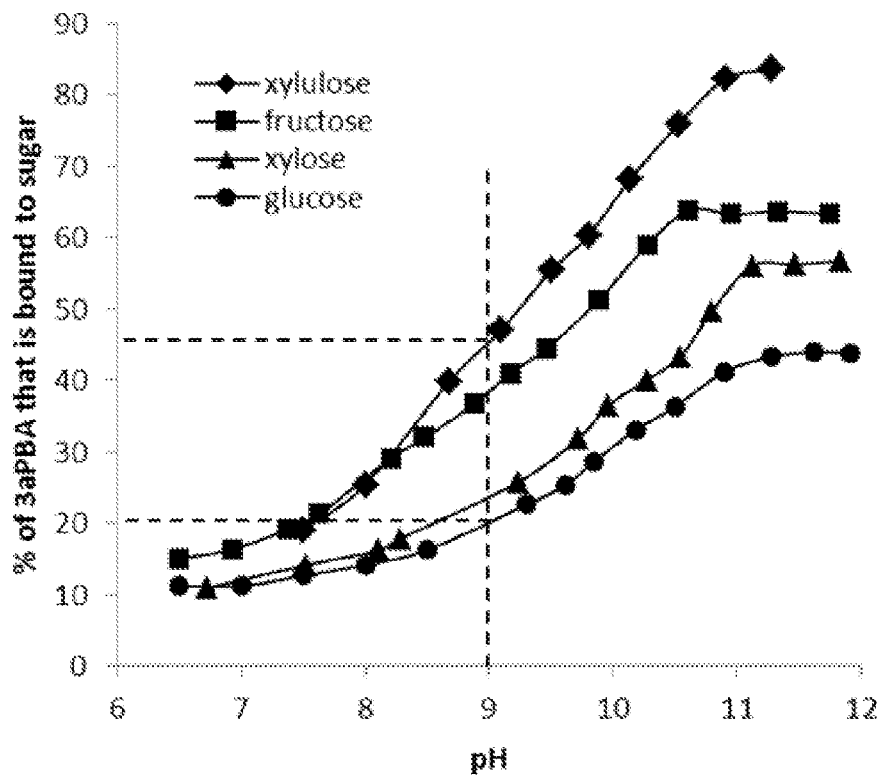
FIG. 11: Graph showing sugar binding to 3aPBA immobilized on beads. Each of the sugars was tested separately for affinity in binding to the CA. Initial molar ratio of immobilized PBA to sugar is 1:1.5. Xylulose affinity to the immobilized CA is clearly higher than the aldose sugars; at pH 9, the equilibrium dissociation constant for glucose is 4-fold higher than for xylulose.

The majority of glucose is not extracted into the organic phase due to the vast affinity difference between glucose and xylulose toward ABA (e.g., see data in FIG. 11). The small quantity of fructose formed co-extracts with the xylulose.

FIG. 3—Step 3: Following the isomerization and extraction in Step 2, the extraction loop is shut down. The hydrolysate remaining in the vessel 30 contains predominantly glucose; the organic phase contains the bulk of the initial xylose in the form of xylulose complexed to ABA.

FIG. 3—Step 4: A low pH aqueous medium 36 in the pH range of 2-4.5 is prepared with the acid HX (where X is the same anion as that of the lipophilic ammonium salt) for stripping of the xylulose from the organic phase generated in Step 3.

FIG. 3—Step 5: The low pH aqueous medium 36 is pumped through another module 38 where it is brought into contact with the xylulose-rich organic phase from Step 3. At the low pH, bound xylulose and a hydroxyl ion are released from the complex into the aqueous phase and the ABA gets converted to its non-ionic conjugate acid (see Eq. 2). At the same time, the $Q^+$ ion that formed the ion pair with the complex will combine with an $X^-$ ion from the aqueous medium to form the lipophilic ammonium salt.

FIG. 3—Step 6: At the end of the stripping process, the concentrated xylulose-rich medium is used for subsequent conversion to product. By controlling the volume of stripping medium used, the concentration of xylulose can be higher than the initial concentration of xylose in the hydrolysate. The regenerated organic phase containing the ABA and the lipophilic ammonium salt can be reused and recycled for the next batch of hydrolysate.

Implementation of Method II—Isomerization Coupled to Selective Simultaneous Extraction and Stripping in a Hollow Fiber Contained Liquid Membrane Contactor (HFCLMC)

Figure 4:
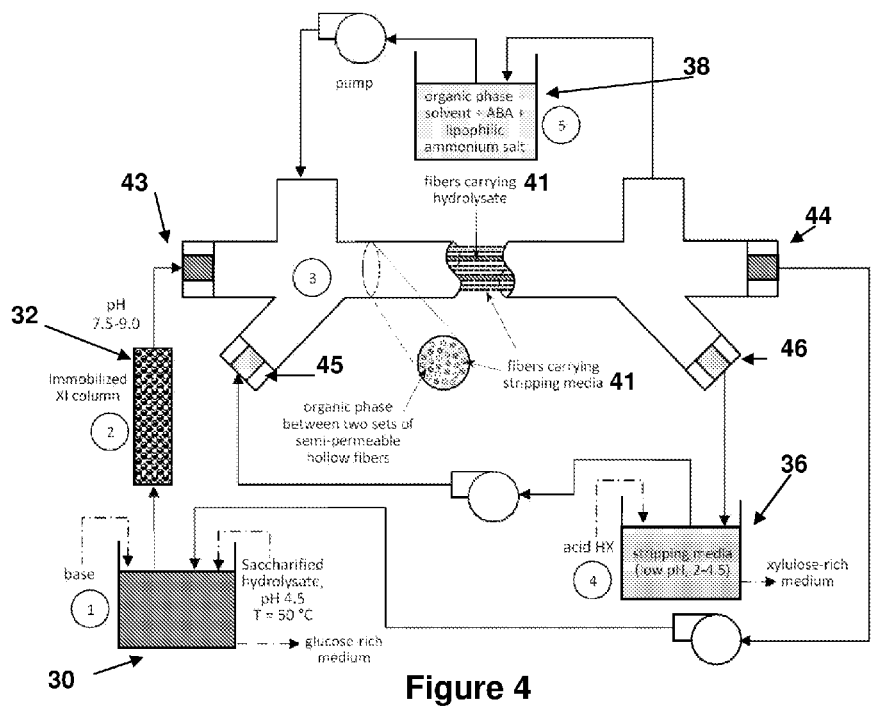
FIG. 4: Schematic diagram showing separation of xylose (in the form of its keto-isomer: xylulose) from a biomass hydrolysate containing a mixture of glucose and xylose. Step 1: biomass hydrolysate initially containing glucose and xylose maintained at a pH of 7.5 to 9.0. Step 2: a jacketed packed bed of immobilized xylose isomerase (XI) particles (200 μm), the temperature of which is maintained at 50° C. Step 3: a hollow fiber contained liquid membrane contactor (HFCLMC) with two sets of co-mingled hollow fibers. Within the HFCLMC, one set of hollow fibers carries the aqueous hydrolysate and the other set carries the stripping solution. Both sets of fibers are surrounded by the organic extraction phase that fills the shell-side of the module. Step 4: low pH aqueous stripping solution that will become enriched in xylulose. Step 5: organic phase that constitutes the contained liquid membrane (this phase has dissolved ABA and a lipophilic ammonium salt). Solid arrows indicate fluid flow paths; dashed arrows represent addition/withdrawal of material at a specific time.

FIG. 4 is a schematic illustration of a HFCLMC system (used in the method shown in FIG. 3) where a shell 40 includes separate sets of microporous hollow fibers that are commingled and well-packed in the shell (e.g., light gray fiber 41 and dark gray fibers 42 in FIG. 4, object 3). The feed hydrolysate from the packed bed reactor 32 is pumped through an input unit 43 of one set of fibers 42 (dark fibers) and out a second unit 44. The stripping solution 36 is fed through a first input unit 45 of the other set of fibers 41 (light gray fibers) and out a second unit 46. Thus, the organic extraction phase is contained in the shell-side space of the HFCLMC device. The pores in the hydrophobic fibers (viz. polypropylene) are filled with the organic phase liquid. The interface between the aqueous phase and the organic phase is maintained at the pore mouths on the input lumen sides of the fibers by adjusting the fluid pressures.

One embodiment of a HFCLMC for the separation of glucose from xylulose and concentration of xylulose is shown in FIG. 4. Saccharified biomass hydrolysate 30 (at pH 4.5 and 50° C.), containing glucose and xylose, is filtered to remove lignin and other particulates and the pH is raised to a value between 7.5 and 9 through addition of a suitable base (see FIG. 4, unit 1).

The hydrolysate is passed through a packed bed reactor 32 containing immobilized XI (or solid acid/base catalyst) (unit 2) where xylose is converted to xylulose. The partially-isomerized hydrolysate flows through the set of dark gray fibers 42 within the HFCLMC (unit 3) where it comes into contact with an immiscible organic phase containing a lipophilic ABA and a quaternary ammonium salt (QX, such as Aliquat® 336) that fills the shell side of the fibers (unit 5). The xylulose formed in the isomerization reaction will be extracted into the organic phase via ester formation with the conjugate base form of the CA coupled to ion pair formation with $Q^+$. This in effect reduces the concentration of "free" xylulose in the hydrolysate, shifting the xylose/xylulose equilibrium in favor of more xylulose formation (Eq. 3).

A low pH aqueous medium 36 (unit 4) in the pH range of 2-4.5 is prepared with the acid HX (where X is the same anion as that of the lipophilic ammonium salt) for stripping of the xylulose from the organic phase in the HFCLMC. This low pH aqueous solution concurrently flows through the second set of fibers 41 (light gray) and also contacts the organic phase contained on the shell side. At the low pH interface, bound xylulose and a hydroxyl ion are released from the complex into the aqueous phase and the ABA gets converted to its non-ionic conjugate acid (see Eq. 2).

At the same time, the $Q^+$ ion that formed the ion pair with the complex will combine with an $X^-$ ion from the stripping medium to form the lipophilic ammonium salt. Thus, xylulose is transported from the high pH to the low pH medium across the contained organic liquid membrane in the device. The transport of xylulose is facilitated through the organic film by the dissolved ABA and QX combination.

As the hydrolysate repeatedly passes through the immobilized XI (or solid acid/base catalyst) column, the extraction of xylulose to the organic phase continues until nearly all of the xylose is isomerized. At the end of the contacting process, xylulose is accumulated in process 36 (unit 4) and glucose remains in the first container 30 (unit 1). By controlling the volume of stripping medium used, the concentration of xylulose can be higher than the initial concentration of xylose in the hydrolysate. The organic phase containing the ABA and the lipophilic ammonium salt can be used repeatedly.

Implementation of Method II—Isomerization Coupled to Selective Solid-Phase Extraction and Stripping The liquid-liquid extraction and stripping systems described in Method II confine the ABA to the organic phase through the addition of the QX compound.

Another, and simpler, method for confining the sugar complexing agent to a second phase is by binding it to a solid support material. In this way, the immobilized CA acts as a solid-phase extraction medium and the overall process operates in a manner similar to the "isomerization coupled to selective liquid-extraction and stripping" described previously.

By immobilizing the sugar complexing agent to a support material, the property of the CA can also be altered to further enhance its selectivity for a specific sugar and alter the pH range over which this binding occurs. Once a sugar has selectively bound to the immobilized CA, it is effectively removed from the hydrolysate medium. Subsequently, the bound sugar can be dislodged from the CA by flushing the support material with a lower pH solution, thereby achieving its separation from the hydrolysate.

By selecting appropriate complexing species, pH and temperature conditions, the present method uses differences in binding affinity of the CA to specific sugars, and selectively removes a single or multiple sugars from a sugar mixture (such as biomass hydrolysate).

This method has the additional advantage that, following separation, the separated sugar(s) is already in the ketose form that is readily amenable to further chemical conversion. Moreover, the separated sugars can be recovered in the form of concentrated solutions.

Figure 5:
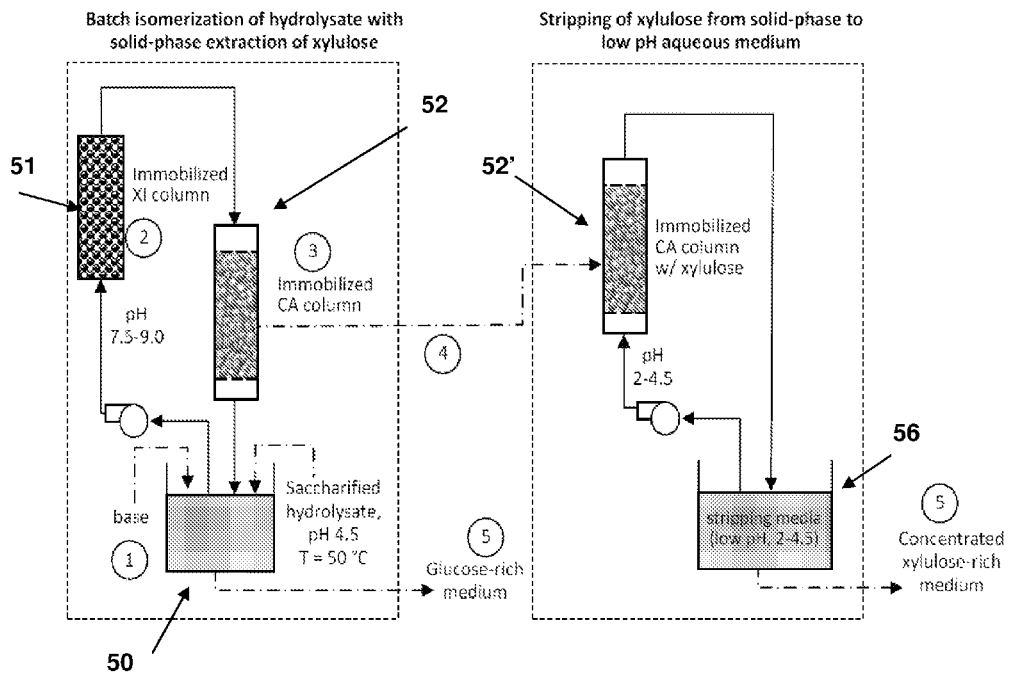
FIG. 5: Schematic diagram showing separating xylose (in the form of its keto-isomer: xylulose) from a biomass hydrolysate containing a mixture of glucose and xylose. Step 1: 250 ml of biomass hydrolysate containing 90 g/l glucose and 30 g/l xylose maintained at a pH of 7.5 to 8.0. Step 2: a jacketed packed bed of immobilized xylose isomerase (XI) particles (200 μm), the temperature of which is maintained at 50° C. Step 3: a packed bed of xylulose complexing-agent bound to a support material. Solid arrows indicate fluid flow paths; dashed arrows represent addition/withdrawal of material at a specific time.

Another embodiment of Method II is shown in FIG. 5 for the specific example of separating xylose (in the form of its keto-isomer, xylulose) from a biomass hydrolysate 50 containing a mixture of glucose and xylose. The biomass hydrolysate 50 is recirculated through a sequence of two packed columns: a first column 51 is a packed bed of immobilized xylose isomerase XI (or solid acid/base catalyst) particles; and a second 52 column is a packed bed of a complexing agent (CA) immobilized on a support material.

The CA and its binding chemistry to the support material are so chosen that at the pH and temperature conditions of the experiment it would only bind to xylulose, and will not bind any appreciable amounts of glucose, xylose or fructose. As the hydrolysate passes through the first (XI) column 51, xylose and a portion of glucose are converted to their corresponding keto-isomers (xylulose and fructose, respectively). As this reaction mixture is routed through the immobilized second (CA) column 52, only the xylulose in the sugar mixture will complex with bound CA sites, thereby lowering the xylulose concentration in the hydrolysate. This reduction of "free xylulose" concentration in the hydrolysate drives the isomerization reaction in the direction of more xylulose formation. This in situ product (xylulose) removal from the reaction mixture allows one to overcome the unfavorable equilibrium ratio of xylose:xylulose for this reaction.

Thus, as the reaction mixture circulates through the two-columns connected in series to the batch vessel 50 containing the hydrolysate, not only will all the xylose in the hydrolysate be converted to xylulose, but it will also attach to the CA in the second (CA) column 52. Hence, at the end of the process, there is a hydrolysate in the batch vessel 50 containing essentially only the C6 sugars.

At this point, the system can be adapted to isolate the immobilized CA column 52 (shown on the right sight of FIG. 5) from the system loop (shown on the left side of FIG. 5) and flush the second (CA) column 52 with a solution 56 of low pH, so the bound xylulose will be released from the CA sites and will accumulate in the low pH carrier medium 56.

This method will also regenerate the immobilized CA column which could now be reused with a fresh batch of biomass hydrolysate. The low pH 2 to 4.5 medium used to dislodge bound-xylulose can be pH adjusted slightly following sugar removal to accommodate fermentation of xylulose to ethanol by native *S. cerevisiae*. By controlling the volume of the carrier solution used to dislodge the bound-xylulose, one can also recover the xylulose solution as a "concentrated" solution. Thus, this method, in addition to separating the xylose from C6 sugars in the form of its keto-isomer, allows us to recover it as a concentrated solution.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein. The methods described herein provides at least the following: enhancement of xylose isomerization with complexing agents; robust immobilization of XI; identification of specific CAs that can display selective affinity toward xylulose at the pH optimum for immobilized XI (or solid acid/base catalyst); isomerization by immobilized XI particles and enhancement of equilibrium conversion with complexing agents that can phase-switch between aqueous and organic phases; extraction and subsequent stripping of xylulose into (and out of) an organic phase containing a CA and a lipophilic salt; immobilization of ABAs on solid supports to implement solid-phase extraction; and, isomerization coupled to selective solid-phase extraction and stripping.

Example 1

Enhancement of Xylose Isomerization with Complexing Agents

The inventors herein designed a jacketed packed bed immobilized XI reactor using commercial Gensweet™ particles to assess the performance of complexing agents on xylose isomerization. Isomerization of xylose was conducted at 50° C. using 50 mL of media containing 10 mM Tris buffer and 30 g/L xylose recirculated at 30 ml/min through the packed bed reactor.

Figure 6:
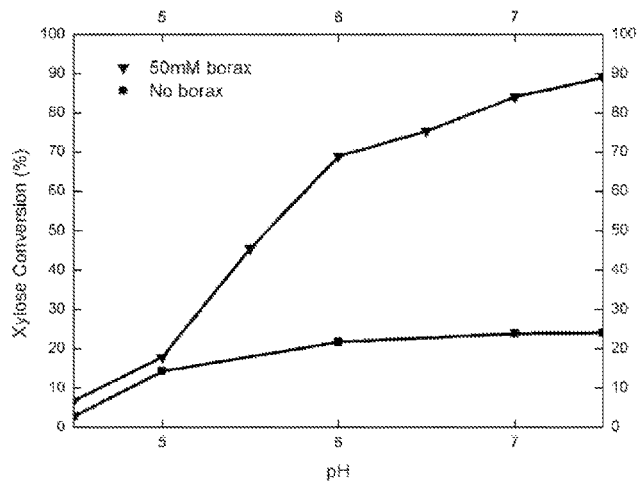
FIG. 6: Graph showing effect of pH on xylose isomerization in the presence of borate. Isomerization was carried out at 50° C. with 30 g/l xylose and sodium tetraborate (borax). Solid triangle: 50 mM sodium tetraborate; solid square: no sodium tetraborate.

While borax as a complexing agent shifts the xylose-xylulose equilibrium towards higher yields of xylulose, due to its water solubility over a wide pH range, borax is not amenable to recovery using the methods described herein. Still, notwithstanding the limitations of borax, the inventors' initial experiments aimed at understanding the role of boronate-ester formation on xylose-xylulose equilibrium shift were conducted with and without borax (50 mM) in the medium. The results of these experiments are summarized in FIG. 6.

In the absence of borax, even at the optimum pH (~7.5-8.5) of the XI the maximum conversion of xylose is less than 30% indicating the extremely unfavorable equilibrium for this reaction. Borax, which preferentially forms boronate esters with xylulose, is able to significantly shift this equilibrium, ultimately reaching near 90% conversion to xylulose. Accordingly, the data in FIG. 6 was used as the baseline while evaluating other complexing agents.

Example 2

Robust Immobilization of XI

In this example, novel covalent binding of XI to functionalized supports are used to achieve robustly immobilized XI. The performance of XI on these supports is evaluated in the presence of 50 mM borax for comparison with the commercial pellets.

The data show results for the robust immobilization of XI. Three functionalized commercial supports, namely Eupergit® C250L, Sepabeads® EP, and Sepabeads® HFA, were used. These supports (beads with ~250 μm diameter) were selected due to their functionalization with oxirane groups and their ability to withstand pH range from 0 to 14 without swelling or shrinking. The oxirane chemistry allows stable covalent binding under mild reaction conditions (neutral and alkaline pH) to several different groups (e.g. amino (primary), hydroxyl, thiol, phenolic and imidazole ones) on enzymes.

Immobilization of soluble XI (SGI, Genencor) on the specific support Sepabeads EP was achieved by contacting excess enzyme in 50 ml of 1.25 M phosphate buffer at pH 8 with 0.94 g beads in a well-stirred batch vessel. Of the three supports, Sepabeads EP provided the most robust immobilization of XI.

Figure 7:
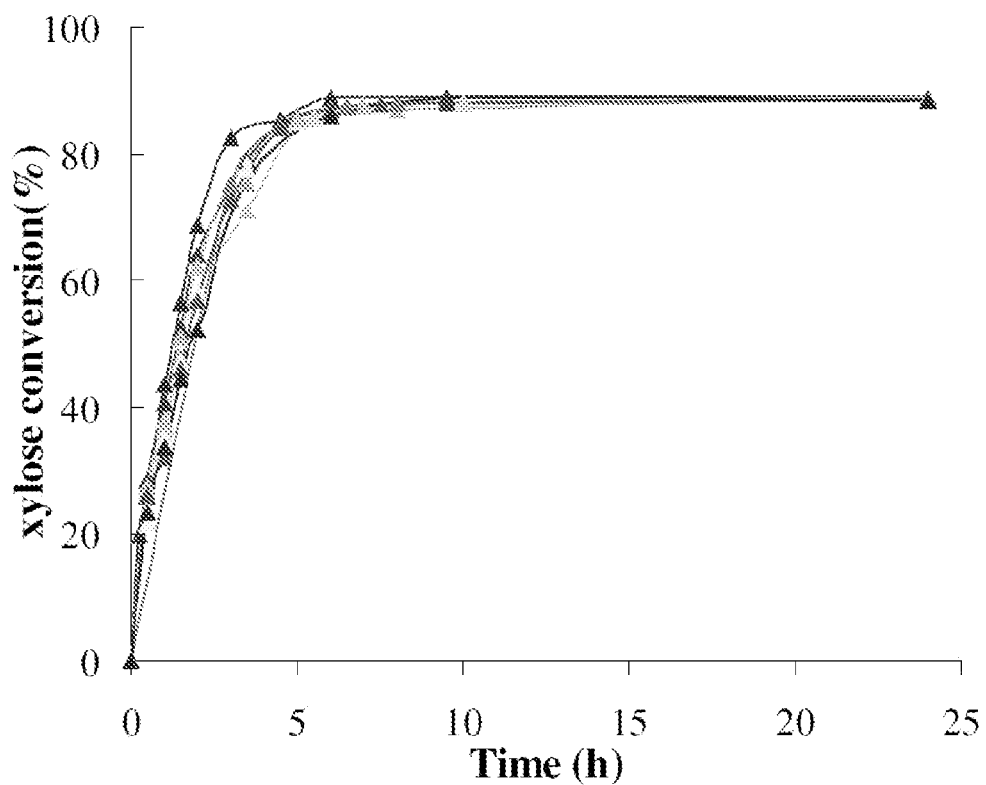
FIG. 7: Graph showing activity of XI immobilized on Sepabead® EP after continuous isomerization of xylose for 10 days. Very little change in the rate of isomerization is noted between individual experiments.

Isomerization was conducted in the same manner as in Example 1. To evaluate robustness (longevity of enzyme activity) of the immobilized XI, isomerization experiments were conducted for varying lengths of time over a 14 day period. The transient concentrations of xylose and xylulose in the reaction media were measured using HPLC to determine the kinetics of the isomerization and hence the activity of the immobilized enzyme. XI immobilized on Sepabeads EP shows remarkable stability and retention of XI activity, as shown in FIG. 7, and thus XI immobilized on Sepabeads EP has great utility.

Example 3

Specific CAs that Display Selective Affinity Toward Xylulose at a pH Optimum for Immobilized XI Biomass hydrolysate medium is a mixture of both C6 and C5 sugars. The XI enzyme is capable of catalyzing aldose-ketose transformations of both glucose and xylose. As such, the inventors herein identified CAs that display higher affinity toward xylulose than fructose, as less CA would be required to achieve high xylulose yields. In some applications, such as cellulosic ethanol, glucose-fructose transformations are inconsequential as yeast strains used for fermentation can use either sugar equally. However, yeast cannot ferment xylose to ethanol. For this scenario, CAs selective to xylulose that can be recovered using Method I or Method II.

Figure 8:
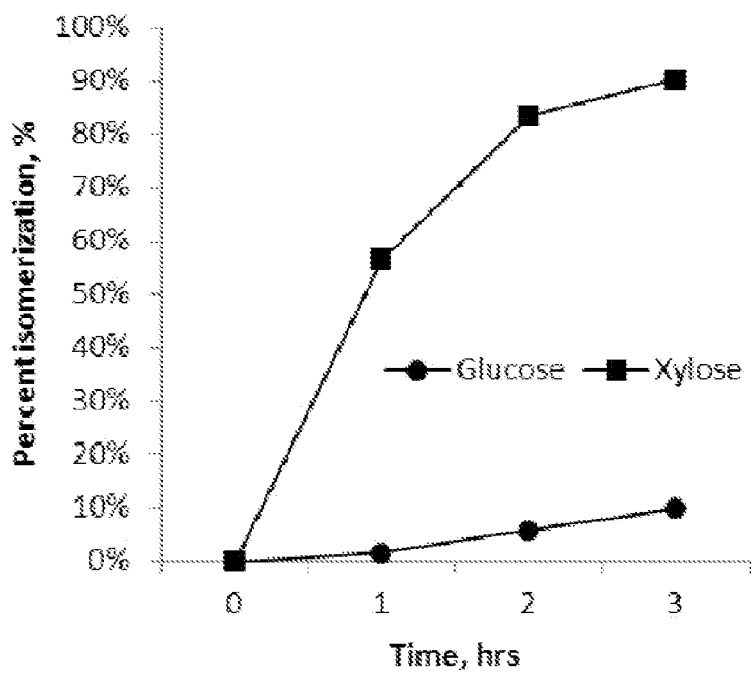
FIG. 8: Graph showing aldose/ketose conversion of glucose (circle) and xylose (square) by GenSweet™ (commercially immobilized XI) in the presence 50 mM borax, a water-soluble CA. Initial concentrations of sugars in hydrolysate were 90 g/l glucose and 17 g/l xylose at pH 7.5 and 50° C.

As shown in FIG. 8, when poplar hydrolysate is isomerized with 50 mM borax as a CA, a significantly higher proportion of xylose is converted to xylulose than glucose to fructose. It is again to be noted, borax is not compatible with the recovery Methods I and II because it stays water-soluble over a wide pH range and is not easily immobilized to a support material.

The inventors determined several CAs that are useful for the schemes described in Methods I and II. The tetrahydroxyborate ions derived from borax are able to efficiently bind to ketose sugars as already seen in Example 1 (see, for example, $B(OH)_4^-$ in FIG. 9).

Figure 9:
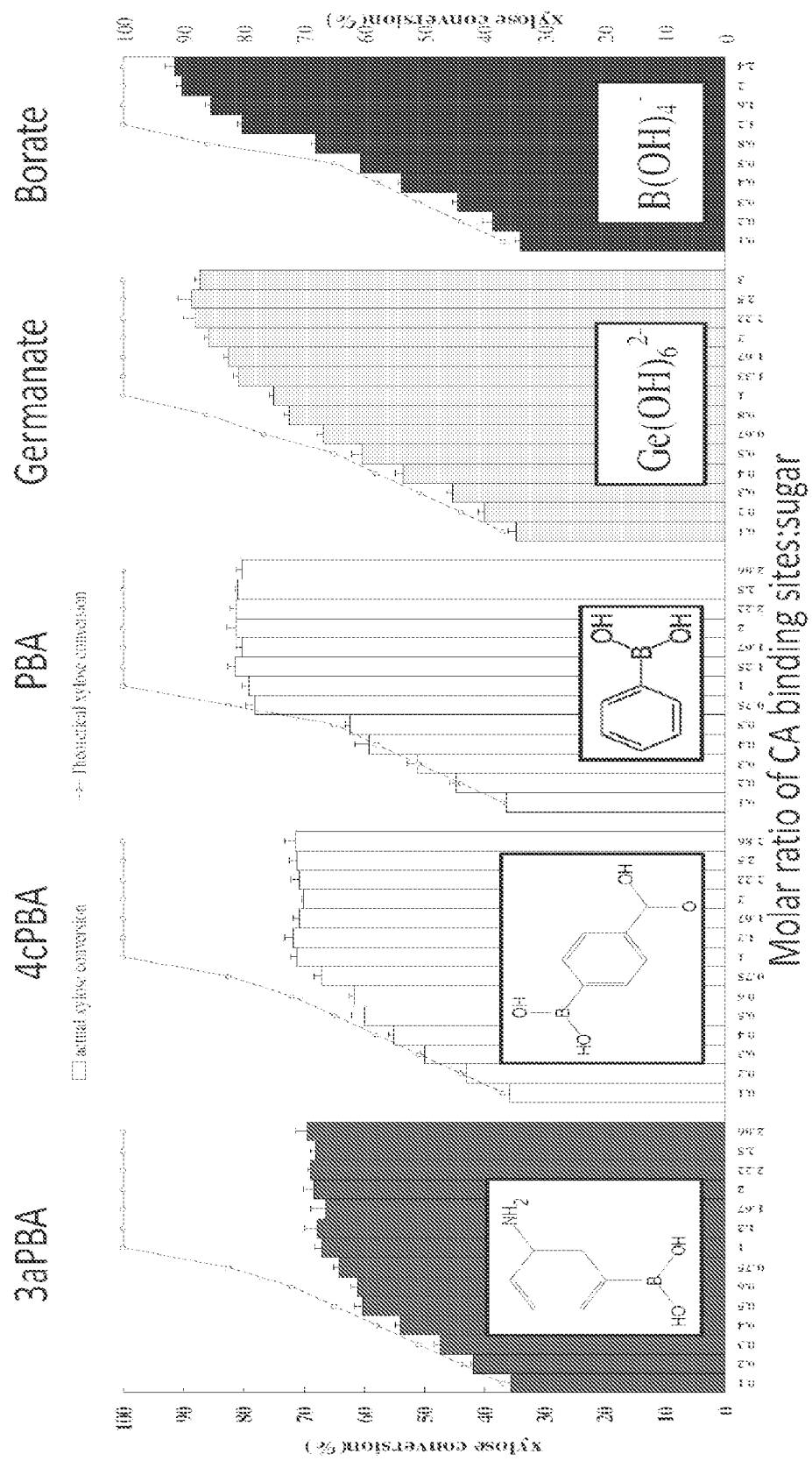
FIG. 9: Graphs showing isomerization with 0.9 g immobilized XI at pH 8. A volume of 50 mL 50 mM Tris-HCl buffer containing 30 mM xylose at 50° C. and shaken at 130 rpm was supplemented with different concentrations of each of the CAs: 3aPBA (3-aminophenyl boronic acid); 4cPBA, PBA, Germanate, Borate. The theoretical line included for each CA shows the maximum possible conversion achievable if all CA present were bound to xylulose.

The inventors also observed that hexahydroxygermanate is also an equally efficient inorganic ketose-sugar selective CA (see, for example, $Ge(OH)_6^{2-}$ in FIG. 9). Borate and germanate are inorganic oxyanions and cannot partition into organic solvents, nor can they be easily covalently-bound to solid substrates. Appreciable solubility in organic solvents can be imparted to borates by converting them to aryl boronic acids (ABAs). ABAs also retain their ability to bind to sugars. The three CAs, in FIG. 9, for example, PBA,

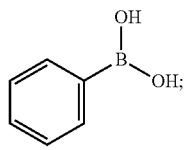

3aPBA,

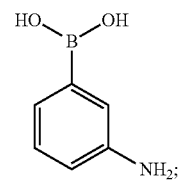

and 4cPBA,

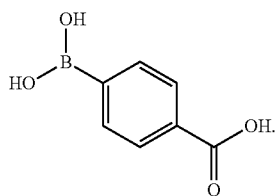

are aryl boronic acids and, as such, are suitable for implementation in Method I and II. It should be noted that to be useful in solid phase extraction, an additional requirement of the ABA is the presence of a functional group on the benzene ring that serve to tether the ABA to a solid support. The amine and carboxyl groups on 3aPBA and 4cPBA serve this purpose.

The ability of each of these CAs to bind sugar varies with pH. While not wishing to be bound by theory, the inventors herein now believe that as the pH increases the proportion of the CA in the conjugate base form will increase. This shift between conjugate acid and base will depend on the difference between the pKa of the specific CA and the pH. Since only the conjugate base forms the tetragonal boronic acid ester, the unbound xylulose concentration in the aqueous phase decreases with increasing pH, shifting the isomerization equilibrium in favor of more xylulose formation. Each of the compounds tested show a significant increase in xylose conversion in the pH range from 7.5 to 8.5 (data not shown). All the data in FIG. 9 were collected at pH 8 for increasing molar ratios of CA-binding sites to sugar. The inorganic oxyanions were able to achieve up to 90% conversion of xylose whereas the aryl boronic acids reached conversions of between 70-80% even when the CA was far in excess of the sugar. This differential performance is likely due to the differences in the pKa's as well as the intrinsic affinity of the individual CAs toward xylulose.

Example 4

Isomerization by Immobilized XI Particles and Enhancement of Equilibrium Conversion with Complexing Agents that can Phase-Switch Between Aqueous and Organic Phases The inventors herein tested the ability of 4cPBA to isomerize xylose in a phase-switching configuration. Appropriate amounts of the organic phase (MIBK) with dissolved 4cPBA, a high pH aqueous phase containing xylose, and immobilized XI pellets were brought together in a shake flask and the three-phase mixture was vigorously stirred overnight. The conversion of xylose to xylulose was compared to a baseline case with the same amount of CA dissolved directly into the aqueous phase at high pH.

4cPBA enhances isomerization by binding to xylulose following its extraction from the MIBK to the aqueous phase. The enhancement seen in this phase-switching mode is within 80% of that seen when it was directly added to the aqueous phase. Results of the experiments are summarized in Table 1 below.

TABLE 1

| Case | CA[1] | Aqueous Phase | Initial composition of organic phase[1] | Xylose conversion | Notes |
| --- | --- | --- | --- | --- | --- |
| 1 | None | 50 ml of 20 mM xylose | None | ~28% | Baseline conversion w/o CA |
|  | 4cPBA | 50 ml of 30 mM xylose + 30 mM 4cPBA | None | ~70% | Baseline conversion w/ 4cPBA |
|  | 4cPBA | 50 ml of 20 mM xylose | 100 ml of 10 mM 4cPBA in MIBK | ~57% | Conversion w/ 4cPBA phase switching |

These experiments illustrate the achievability of phase-switching to enhance xylose isomerization. Immobilized XI was added to the aqueous phase at pH 8 with or without 4cPBA in a shake flask. For the phase switching experiments, the CA was dissolved in methyl-isobutyl-ketone (MIBK) and the immiscible organic phase was mixed vigorously with the aqueous sugar solution. Experiments were run overnight to ensure equilibrium conversion. The CA to xylose molar ratios used was 1:1.

4cPBA does not dissolve in aqueous solution at low pH. Accordingly, lowering the pH of the shake flask contents at the end of the experiment will release the xylulose bound to the 4cPBA and 4cPBA will migrate back to the MIBK phase, leaving free xylulose behind. Thus, this experiment provides proof for the phase-switching method of enhancing isomerization of xylose by the CA.

Addition of a lipophilic ammonium salt QX to the organic phase along with ABA prevents the migration of ABA into the aqueous phase even at high pH. Instead, the xylulose is extracted into the organic phase as described in Method II. In this embodiment, removal of xylulose from the aqueous medium drives the isomerization towards more xylulose formation. Further, contacting the organic phase with a small quantity of a low pH aqueous stripping solution will release the xylulose into the aqueous medium as a concentrated sugar solution (see Table 2 below). This mode of operation corresponds to liquid-liquid extraction followed by stripping (Method II). These data also form the basis for the implementation of Method II in a HFCLMC configuration.

Further experiments, as shown in Table 2 below, illustrate the achievability of extraction followed by stripping to enhance xylose isomerization and recovery.

TABLE 2

| CA | aqueous phase | Initial composition of organic phase | Composition of extracted sugar solution |
|---|---|---|---|
| None | 50 ml of 20 mM xylose | None | ~28% xylulose |
| N2B | 100 ml of 20 mM xylose | 100 ml of n-hexane/ 1-octanol, 150 mM Aliquat ® 336, N2B | ~77% xylulose |

These experiments illustrate the achievability of extraction followed by stripping to enchance xylose isomerization and recovery. Immobilized XI was added to the aqueous phase at pH 8.5 with or without naphthalene-2-boronic acid (N2B) in shake flask. For the extraction experiments, the N2B was dissolved in an 85:15 v/v ratio of n-hexane to 1-octanol containing 150 mM Aliquat ® 336. The immiscible organic phase was mixed vigorously with the aqueous sugar solution for 9 hrs. The stripping experiments were run by contacting the sugar-laden organic phase with 0.5 M HCl (pH ~ 0.3) for 30 mins, The N2B-to-sugar molar ratios tested were ≥ 2.5:1.

Example 5

Immobilization of ABAs on Solid Supports to Implement Solid-Phase Extraction

Figure 10:
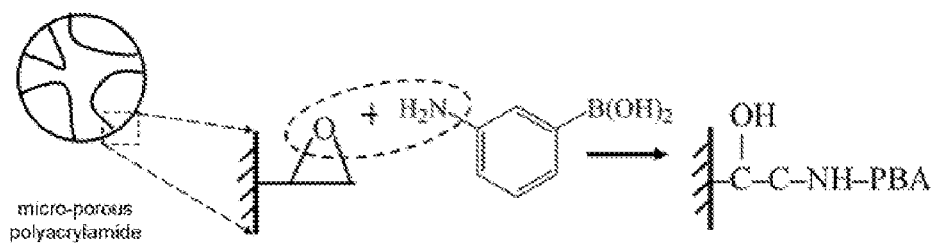
FIG. 10: Schematic illustration depicting immobilization of 3aPBA on Sepabeads-EP®.

As noted in Example 3, both 4cPBA and 3aPBA possess pendant groups that enable their attachment to a functionalized solid support. The Sepabead® EP beads used for the immobilization of XI also form a suitable support for immobilization of 3aPBA. The oxirane group on the support covalently bonds the amine group of the 3aPBA by epoxide ring-opening as shown in FIG. 10.

Through experiments performed over a range of pH values and sodium phosphate buffer concentrations, the inventors determined that the useful conditions for immobilization of 3aPBA on the Sepabead® EP were pH 8 and 1 M sodium phosphate buffer at 25° C. In one embodiment, Sepabead® EP beads were contacted with the buffer containing 3aPBA in a molar ratio of oxirane to amine of 1:2 for 24 hrs. Binding of 3aPBA was followed indirectly by monitoring the concentration of 3aPBA in the buffer with UV absorbance spectroscopy at 295 nm. At the end of the experiment, the beads were washed thoroughly with DI water to remove any non-covalently associated 3aPBA. Based on mass balances, it was determined that under the conditions specified, all of the oxirane sites were covalently attached to 3aPBA.

The inventors investigated the affinity of the immobilized CA to the four sugars: glucose, fructose, xylose and xylulose. FIG. 11 shows the observed degree of binding of each sugar to the CA as a function of pH. The distinct features discernable from the data are that ketoisomers display higher binding capacity to CA than their aldose counter-parts for both C6 and C5 sugars. Among all the sugars xylulose displays the highest affinity towards the CA.

In biomass hydrolysate glucose and xylose are the two predominant C6 and C5 sugars; when the hydrolysate at a pH of 9 is circulated through an immobilized CA column, both sugars bind to CA to about the same extent (see FIG. 11, red ($4^{th}$) and green ($3^{rd}$) lines) and no effective separation of sugars can be achieved although some recovery of both sugars is possible (~20% of CA complexed to sugar, see FIG. 11).

However, if the hydrolysate is passed through an immobilized xylose isomerase (XI) column prior to the CA column (see FIG. 5), the resulting keto-isomer of xylose (xylulose) displays much higher affinity to immobilized CA compared to glucose (see FIG. 11, red ($4^{th}$) and blue ($1^{st}$) lines), leading to a much better separation from glucose.

As can be seen from the schematic illustration shown in FIG. 5, this method of sequentially passing the sugar mixture though the XI and CA columns also overcomes the unfavorable xylose:xylulose equilibrium by continuously removing xylulose from the sugar mixture as it is formed via its attachment to the CA. It is of interest to note that in this system, the hydrolysate pH (~9) is not very different from the optimal pH of commercially available XI, and thus the conversion of xylose to xylulose is not compromised. At the end of the recirculation process, the xylulose bound to the CA column can be easily recovered as a concentrated xylulose solution by simply flushing the CA column with a small quantity of aqueous solution at low pH (see FIG. 5). Thus, the method not only provides an improved method for separating glucose from xylose, but also converts the latter to its more valuable isomer, xylulose. These concentrated xylulose streams can be fermented using native microbial strains, at high productivity rates, to fuels such as ethanol and chemicals such as succinic and fumaric acids.

Example 6

Isomerization Coupled to Selective Solid-Phase Extraction and Stripping

Using the Method II illustrated in FIG. 5, 150 ml of a xylose solution in 50 mM sodium phosphate at pH 8.5 and 50° C. was circulated through the packed bed isomerization column containing 2.7 g of immobilized XI pellets at 15 ml/min. The sugar was partially pre-isomerized to xylulose overnight prior to connecting the immobilized 3aPBA column (pellets containing 6 mmol of 3aPBA) into the loop; the media was then circulated for an additional 6 hours. Following isomerization and binding of the xylulose to the immobilized 3aPBA column, the 3aPBA column was disconnected from the loop and the bound sugars were extracted into a second vessel by flushing with 50 mL of 50 mM sodium citrate elution buffer at a pH of 3.

Figure 12:
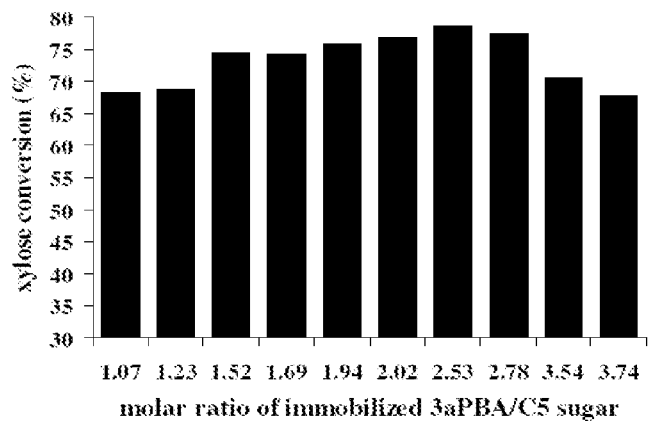
FIG. 12: Graph showing xylose isomerization result with different molar ratio of immobilized 3aPBA and C5 sugar at pH 8.5 and 50° C.

As shown in FIG. 12, the percentage of xylulose in the solution stripped from the 3aPBA column is about 70-80%, depending on the 3aPBA to sugar molar ratio. These data show the feasibility of separating xylulose from aldose sugars; by properly optimizing the volume of low pH stripping solution, the concentration of xylulose in the final strip solution can be maximized.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for converting an aldose in a biomass hydrolysate to its ketose isomer, comprising:

adjusting a pH of a saccharified biomass hydrolysate containing one or more aldose sugars to a value between about 7.5 and about 9, to produce a pH-adjusted hydrolysate;

contacting the pH-adjusted hydrolysate with an isomerization catalyst, wherein at least a portion of the aldose sugar in the pH-adjusted hydrolysate is converted to its ketose isomer, to produce an isomerized hydrolysate;

contacting the ketose isomer in the isomerized hydrolysate with an aryl boronic acid (ABA) at a pH in the range of from 7.5 to 8.5 to form a complex of ketose-conjugate base form of the ABA; wherein the contacting comprises bringing the isomerized hydrolysate into contact with an immiscible organic phase that dissolves the ABA and a lipophilic salt (QX), and allowing the ketose in the isomerized hydrolysate to be extracted into the immiscible organic phase via ester formation with a conjugate base form of the ABA that is coupled via ion pair formation with $Q^+$, thereby reducing the concentration of ketose in the isomerized hydrolysate and forming a ketose-rich organic phase, in turn shifting the aldose/ketose equilibrium in favor of more ketose formation in the pH-adjusted hydrolysate;

preparing a low pH medium having a pH in the range of from about 2 to about 4.5, that contains an acid HX, wherein X is the same anion as X in the lipophilic salt (QX);

bringing the low pH medium into contact with the ketose-rich organic phase; wherein, at the low pH, the ketose and hydroxyl ions are released into the low pH medium and the ABA is converted to its non-ionic conjugate acid; and, wherein, at the same time, the $Q^+$ ion that formed the ion pair combines with an $X^-$ ion from the low pH medium to reform the lipophilic salt; and recovering the ketose from the organic phase into the low pH medium as a concentrated ketose-rich solution.

2. The method of claim 1, including controlling the volume of the low pH medium such that the concentration of ketose in the ketose-rich medium is higher than the initial concentration of aldose in the hydrolysate.

3. The method of claim 1, further including reusing the organic phase containing the ABA and the lipophilic salt for a subsequent batch of hydrolysate.

4. The method of claim 1, wherein the steps of contacting the ketose isomer in the isomerized hydrolysate with ABA, and bringing the low pH medium into contact with the ketose-rich organic phase, are carried out using a micro-porous hollow fiber contactor.

5. The method of claim 4, wherein the micro-porous hollow fiber contactor comprises a shell having a first set of porous hollow fibers adapted for carrying the isomerized hydrolysate; and a second set of porous hollow fibers adapted for carrying the low-pH medium;

the shell being configured for containing the organic extraction phase in a shell-side space substantially surrounding the first and second sets of fibers.

6. The method of claim 5, wherein the ketose is transported from the hydrolysate to the immiscible organic phase and from the organic phase to the low-pH medium, wherein the transport of the ketose is facilitated by ABA and QX combination dissolved in the immiscible organic phase.

7. The method of claim 5, wherein the first and second sets of micro-porous hollow fibers are commingled within the shell.

8. The method of claim 5, wherein the saccharified biomass hydrolysate contains glucose and xylose, and the method comprises:

passing the hydrolysate through a packed bed reactor containing immobilized xylose isomerase (XI) or solid acid/base catalyst;

allowing the isomerized hydrolysate to flow through the first set of fibers within the micro-porous hollow fiber contactor, the isomerized hydrolysate coming into contact with the immiscible organic phase containing lipophilic ABA and a lipophilic salt (QX) that fills the shell;

extracting the xylulose in the isomerized hydrolysate, wherein the pH of the isomerized hydrolysate is in the range of from 7.5 to 8.5, into the organic phase via ester formation with a conjugate base form of the ABA coupled by ion pair formation with $Q^+$, thereby reducing concentration of xylulose in the hydrolysate, and shifting the xylose/xylulose equilibrium in favor of more xylulose formation;

concurrently with the extracting, allowing the low pH medium to flow through the second set of fibers and contact the organic phase contained on the shell side; whereby:

the xylulose and hydroxyl ions attached to the ABA are released into the low pH medium, the ABA is re-converted to its non-ionic conjugate acid, and the $Q^+$ ion, which formed the ion pair with ABA, combines with an $X^-$ ion from the low pH medium to re-form the lipophilic salt.

9. The method of claim 1, including selecting an ABA having a property to enhance selectivity for a specific sugar.

10. The method of claim 1, further including controlling the volume of the low pH medium such that the ketose concentration in the recovered solution is higher than the aldose concentration in the saccharified biomass hydrolysate.

11. The method of claim 1, wherein both glucose and xylose from the hydrolysate are simultaneously isomerized by the isomerization catalyst into ketoses, the ketoses are extracted into the organic phase via binding to the ABA and QX, and the ketoses are recovered from the organic phase via back-extraction into the low pH medium while leaving behind other inhibitory compounds in the biomass hydrolysate.

12. The method of claim 1, wherein a micro-porous hollow fiber contactor physically separates the ketose-rich organic phase from the low pH medium during the ketose recovery.

13. The method of claim 1, wherein the step of contacting the pH-adjusted hydrolysate with an isomerization catalyst comprises passing the pH-adjusted hydrolysate through a packed bed reactor containing the isomerization catalyst, wherein the isomerization catalyst facilitates conversion of glucose to fructose.

14. The method of claim 1, wherein the pH of the recovered ketose is adjusted slightly to a pH suitable for converting the ketose to lactic acid, succinic acid, or fumaric acid by native microorganisms.

15. The method of claim 1, wherein the isomerization catalyst preferentially isomerizes xylose into xylulose compared to glucose into fructose, the ABA preferentially binds to ketoses compared to aldoses, and the system is used to separate C5 sugars from C6 sugars.

16. The method of claim 1, wherein the pH of the recovered ketose corresponds to a pH suitable for dehydration of the ketose to furans via an acid-catalyzed chemical reaction.

17. The method of claim 1, wherein the isomerization catalyst comprises xylose isomerase (XI) particles that facilitate the isomerization of both glucose and xylose.

18. The method of claim 1, comprising:

a first micro-porous hollow fiber contactor having a lumen side and a shell side, wherein the hydrolyzate flows through the lumen-side in the first micro-porous hollow fiber contactor and the immiscible organic phase flows through the shell-side; and a second micro-porous hollow fiber contactor that physically separates the ketose-rich organic phase from the low pH medium during ketose recovery.

19. The method of claim 1, wherein the saccharified biomass hydrolysate is a lignocellulosic biomass hydrolysate.

20. The method of claim 19, wherein one or more of the ABA, the pH, and temperature of the hydrolysate, are altered to selectively isomerize and extract one or more specific sugars.

21. The method of claim 1, wherein the ABA is present in an immiscible organic phase that is physically separated by a permeable device from the isomerized hydrolysate, the permeable device allowing transport of the sugar from the isomerized hydrolysate into the immiscible organic phase, while substantially preventing dispersion of the immiscible organic phase in the isomerized hydrolysate.

22. The method of claim 7, wherein the immiscible organic phase comprises one or more of octanol, ethyl acetate, dichloromethane, o-nitrophenyl octyl ether (NPOE), or diethyl ether.

23. The method of claim 21, wherein the permeable device is a micro-porous hollow fiber contactor.

24. The method of claim 1, wherein the step of contacting the pH-adjusted-hydrolysate with an isomerization catalyst comprises passing the pH-adjusted hydrolysate through a packed bed reactor containing the isomerization catalyst, wherein the isomerization catalyst facilitates conversion of xylose into xylulose.

25. The method of claim 24, wherein the packed bed reactor is connected in a loop to a micro-porous hollow fiber contactor having a shell side and a fiber side, such that the hydrolysate flows through the packed bed and the fiber side of the micro-porous hollow fiber contactor, and the ketose is extracted from the hydrolysate to the immiscible organic phase on the shell side of the micro-porous hollow fiber contactor.

26. The method of claim 1, including: selecting the ABA such that, at selected pH and temperature conditions, the ABA mainly binds to xylulose, and does not bind to any appreciable amounts of glucose, xylose, or fructose.

27. The method of claim 1, including circulating the hydrolysate through at least a first column comprised of a packed bed of immobilized xylose isomerase (XI), and through a vessel having an ABA-enriched phase therein.

28. The method of claim 1, wherein the pH of the recovered ketose is a pH suitable for converting the ketose to ethanol by native *S. cerevisiae* or other native microorganisms.

29. The method of claim 1, including controlling a volume of the low pH medium sufficient to recover the ketose as a concentrated solution.

30. The method of claim 1, including separating xylose from other C6 sugars as its keto-isomer and allowing for the recovery of xylulose as a concentrated solution.

31. The method of claim 1, comprising passing the isomerized hydrolysate and the ABA containing organic phase through a micro-porous hollow fiber contactor.

32. The method of claim 1, wherein the ABA is selected from the group consisting of PBA, 3aPBA, 4cPBA, naphthalene-2-boronic acid (N2B), and 4-biphenylboronic acid.

33. The method of claim 1, wherein the ABA has the formula Ar—B(OH)$_2$, where Ar represents an unsubstituted or substituted aryl group.

34. The method of claim 33, wherein the ABA comprises one or more of the aryl groups: 4-PhC$_6$H$_4$—; 4-MeC$_6$H$_4$—, where Me is methyl; 2-iPrC6H4-, where iPr is isopropyl; 2-naphthyl; 3-BnOC$_6$H$_4$—, where Bn is benzyl; 4-MeO$_2$CC$_6$H$_4$—, where Me is methyl; and 4-pyridinyl.

35. The method of claim 33, wherein the ABA comprises a diboronic acid that exhibits a higher selectivity toward ketose binding compared to monoboronic acids.

36. The method of claim 33, wherein the ABA comprises a multi-dentate boronic acid carrier.

37. The method of claim 36, wherein the ABA comprises one or more of:

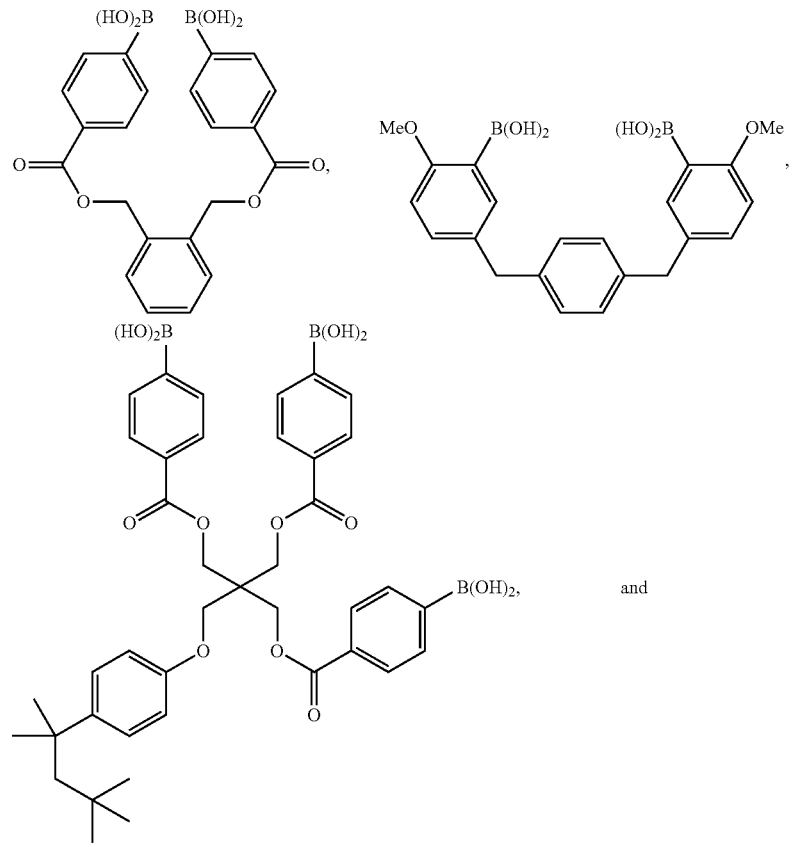

-continued

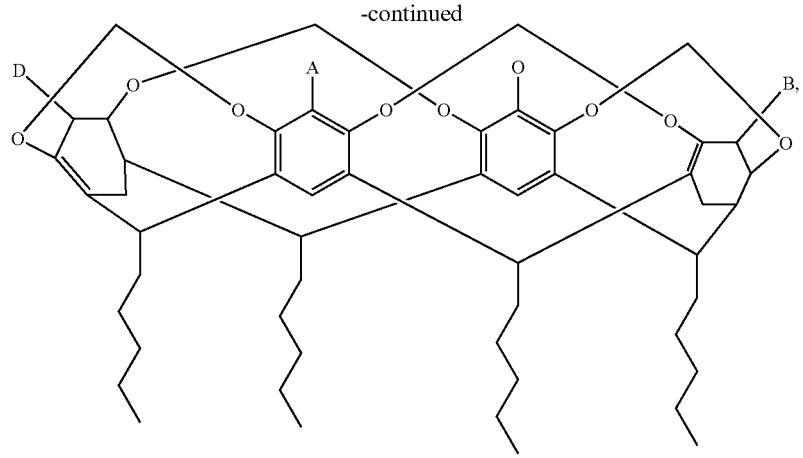

wherein A and C are B(OH)$_2$, and B and D are H groups.

38. The method of claim 1, wherein the ABA comprises a hydrophobic substituted aryl boronic acid.

39. The method of claim 38, wherein the ABA comprises:

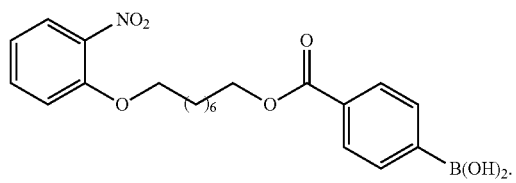

40. The method of claim 38, wherein the hydrophobic substituted aryl boronic acid is used in a liquid-liquid extraction followed by stripping or micro-porous hollow fiber contactor implementation.

* * * * *

UNITED STATES PATENT AND TRADEMARK OFFICE
CERTIFICATE OF CORRECTION

PATENT NO. : 9,242,222 B2  
APPLICATION NO. : 13/641849  
DATED : January 26, 2016  
INVENTOR(S) : Sasidhar Varanasi, Patricia Relue and Bin Li Page 1 of 1

It is certified that error appears in the above-identified patent and that said Letters Patent is hereby corrected as shown below:

Claims

Column 29, Claim 37, Line 1, delete " 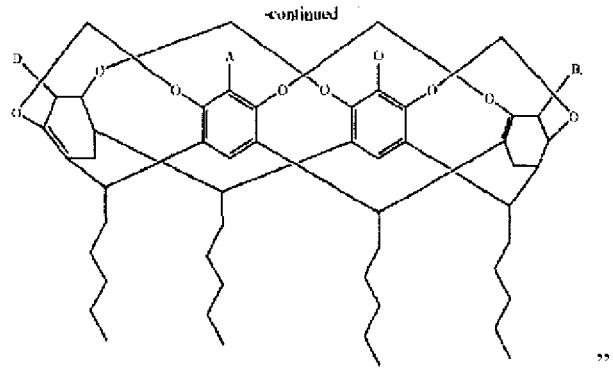 "

and insert -- 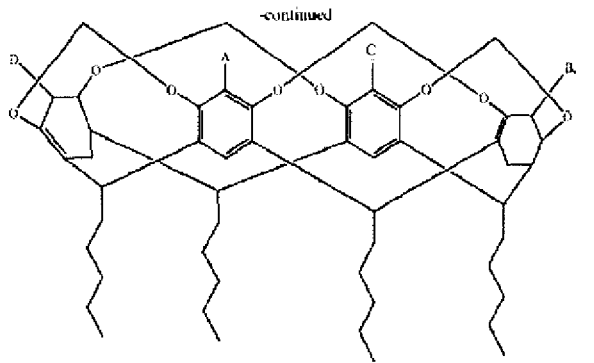 --

Signed and Sealed this  
Twenty-sixth Day of April, 2016

Michelle K. Lee  
*Director of the United States Patent and Trademark Office*